(12) United States Patent
Allman et al.

(10) Patent No.: US 9,447,467 B2
(45) Date of Patent: Sep. 20, 2016

(54) METHODS FOR OBTAINING FETAL GENETIC MATERIAL

(75) Inventors: Richard Allman, Wyndham Vale (AU); Debbie Mantzaris, Avondale Heights (AU); Eduardo Vom, Richmond (AU); Craig Matthew Lewis, Eltham (AU)

(73) Assignee: GENETIC TECHNOLOGIES LIMITED (AU)

( * ) Notice: Subject to any disclaimer, the term of this patent is extended or adjusted under 35 U.S.C. 154(b) by 837 days.

(21) Appl. No.: 13/265,485

(22) PCT Filed: Apr. 20, 2010

(86) PCT No.: PCT/AU2010/000438
§ 371 (c)(1),
(2), (4) Date: Feb. 22, 2012

(87) PCT Pub. No.: WO2010/121294
PCT Pub. Date: Oct. 28, 2010

(65) Prior Publication Data
US 2012/0149014 A1 Jun. 14, 2012

Related U.S. Application Data

(60) Provisional application No. 61/171,334, filed on Apr. 21, 2009.

(51) Int. Cl.
G01N 33/483 (2006.01)
C12Q 1/68 (2006.01)
G01N 33/50 (2006.01)
C12N 15/10 (2006.01)
G01N 15/10 (2006.01)

(52) U.S. Cl.
CPC ......... *C12Q 1/6879* (2013.01); *C12N 15/1003* (2013.01); *C12Q 1/6806* (2013.01); *G01N 33/483* (2013.01); *G01N 33/5076* (2013.01); *C12Q 2600/156* (2013.01); *G01N 2015/1006* (2013.01)

(58) Field of Classification Search
CPC .............. C12Q 1/6879; C12Q 1/6806; C12Q 2600/156; C12N 15/1003; G01N 33/5076; G01N 33/483; G01N 2015/1006
USPC ......... 435/6, 7.21, 366, 286.5, 287.3, 288.6; 436/10, 17, 161, 162, 174, 175, 177, 436/178
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,528,267 A | 7/1985 | Calenoff et al. |
| 4,675,286 A | 6/1987 | Calenoff |
| 4,765,737 A | 8/1988 | Harris et al. |
| 4,835,098 A | 5/1989 | Orr et al. |
| 4,862,899 A | 9/1989 | Bucaro |
| 4,906,561 A | 3/1990 | Thornthwaite |
| 4,987,086 A | 1/1991 | Brosnan et al. |
| 4,988,617 A | 1/1991 | Landegren et al. |
| 5,153,117 A | 10/1992 | Simons |
| 5,242,794 A | 9/1993 | Whiteley et al. |
| 5,447,842 A | 9/1995 | Simons |
| 5,447,864 A | 9/1995 | Raybuck et al. |
| 5,494,810 A | 2/1996 | Barany et al. |
| 5,503,981 A | 4/1996 | Mueller et al. |
| 5,541,072 A | 7/1996 | Wang et al. |
| 5,641,870 A | 6/1997 | Rinderknecht et al. |
| 5,731,156 A | 3/1998 | Golbus et al. |
| 5,750,339 A | 5/1998 | Smith |
| 5,798,276 A | 8/1998 | Haugland et al. |
| 5,804,380 A | 9/1998 | Harley et al. |
| 5,830,912 A | 11/1998 | Gee et al. |
| 5,969,157 A | 10/1999 | Vicenzi |
| 6,059,735 A | 5/2000 | Sgro |
| 6,130,101 A | 10/2000 | Mao et al. |
| 6,162,931 A | 12/2000 | Gee et al. |
| 6,166,178 A | 12/2000 | Cech et al. |
| 6,221,596 B1 | 4/2001 | Yemini et al. |
| 6,258,540 B1 | 7/2001 | Lo et al. |
| 6,582,938 B1 | 6/2003 | Su et al. |
| 6,813,008 B2 | 11/2004 | Fein et al. |
| 6,927,028 B2 | 8/2005 | Dennis et al. |
| 6,949,355 B2 | 9/2005 | Yamanishi et al. |

(Continued)

FOREIGN PATENT DOCUMENTS

AU    1998/65074    9/1998
DE    102005007185    8/2006

(Continued)

OTHER PUBLICATIONS

GenBank Accession No. AAC51724, Aug. 28, 1997, 2 pages.
GenBank Accession No. NM_003219, Oct. 26, 2004, 27 pages.
"Telomere PNA Fish Kit/Cy3—2nd edition," DakoCytomation Denmark A/S, 2004, 10 pages.
Apps et al., "Human leucocyte antigen (HLA) expression of primary trophoblast cells and placental cell lines, determined using single antigen beads to characterize allotype specificities of anti-HLA antibodies," Immunology, 2009, vol. 127, Iss. 1, pp. 26-39.
Bussel et al., "Antenatal Treatment of Neonatal Alloimmune Thrombocytopenia", The New England Journal of Medicine 319:1374-1378, Nov. 24, 1988.

(Continued)

*Primary Examiner* — Gail R Gabel
(74) *Attorney, Agent, or Firm* — Sheridan Ross P.C.

(57) ABSTRACT

The present invention relates to a method of enriching fetal nuclei from a sample. Enriched fetal nuclei can be used in a variety of procedures including, detection of a trait of interest such as a disease trait, or a genetic predisposition thereto, gender typing and parentage testing.

19 Claims, 3 Drawing Sheets

(56) References Cited

U.S. PATENT DOCUMENTS

Figure 1:
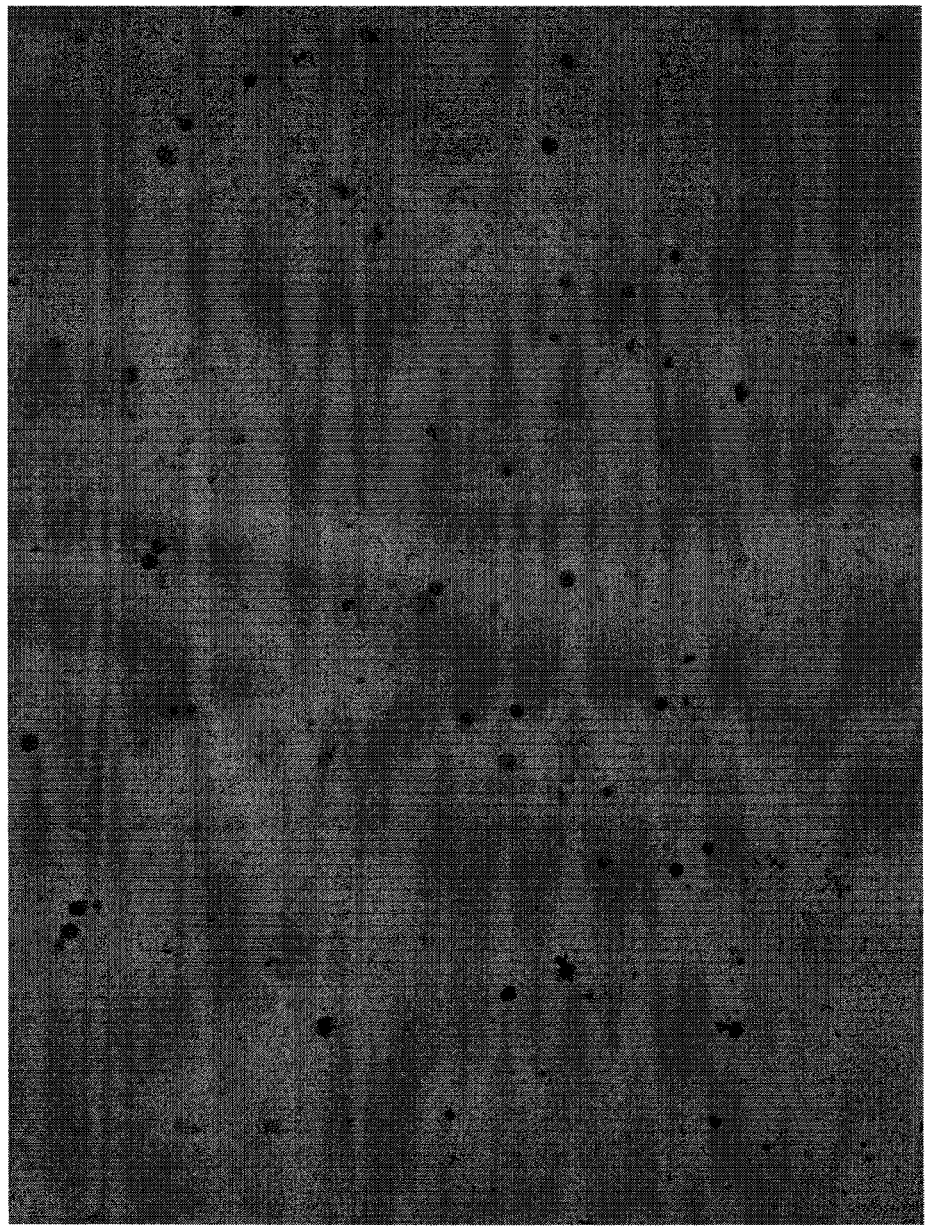

| | | | |
|---|---|---|---|
| 7,083,924 B2 | 8/2006 | Hulten | |
| 7,166,443 B2 | 1/2007 | Walker et al. | |
| 7,439,062 B2 | 10/2008 | Bhatt et al. | |
| 7,785,898 B2 | 8/2010 | Bohmer | |
| 8,137,912 B2 | 3/2012 | Kapur et al. | |
| 8,585,971 B2 * | 11/2013 | Huang et al. | 422/73 |
| 2001/0051341 A1 | 12/2001 | Lo et al. | |
| 2002/0006621 A1 | 1/2002 | Bianchi | |
| 2002/0045176 A1 | 4/2002 | Lo et al. | |
| 2002/0137088 A1 | 9/2002 | Bianchi | |
| 2003/0013123 A1 | 1/2003 | Mahoney et al. | |
| 2003/0044388 A1 | 3/2003 | Dennis et al. | |
| 2003/0211522 A1 | 11/2003 | Landes et al. | |
| 2004/0126796 A1 | 7/2004 | Carlson et al. | |
| 2006/0148075 A1 | 7/2006 | Feinberg et al. | |
| 2007/0134658 A1 | 6/2007 | Bohmer | |
| 2007/0275362 A1 | 11/2007 | Edinger et al. | |
| 2008/0071076 A1 | 3/2008 | Hahn et al. | |
| 2008/0176237 A1 | 7/2008 | Bhatt et al. | |
| 2009/0053719 A1 | 2/2009 | Lo et al. | |
| 2009/0155776 A1 | 6/2009 | Lo et al. | |
| 2009/0305236 A1 | 12/2009 | Boehmer et al. | |
| 2010/0035246 A1 * | 2/2010 | Lushi et al. | 435/6 |
| 2011/0027795 A1 * | 2/2011 | Mantzaris et al. | 435/6 |
| 2012/0122091 A1 | 5/2012 | Vom et al. | |
| 2012/0315633 A1 | 12/2012 | Mantzaris et al. | |
| 2012/0329667 A1 | 12/2012 | Allman et al. | |
| 2013/0171650 A1 | 7/2013 | Bohmer | |
| 2013/0295561 A1 | 11/2013 | Boehmer et al. | |

FOREIGN PATENT DOCUMENTS

| | | |
|---|---|---|
| EP | 0239400 | 9/1987 |
| EP | 0363196 | 4/1990 |
| EP | 0414469 | 2/1991 |
| EP | 0944829 | 9/1999 |
| JP | H05-506114 | 9/1993 |
| JP | H10-234384 | 9/1998 |
| JP | H11-507839 | 7/1999 |
| WO | WO 91/14768 | 10/1991 |
| WO | WO 91/16452 | 10/1991 |
| WO | WO 94/07921 | 4/1994 |
| WO | WO 95/03431 | 2/1995 |
| WO | WO 96/01835 | 1/1996 |
| WO | WO 97/14028 | 4/1997 |
| WO | WO 97/15687 | 5/1997 |
| WO | WO 98/26284 | 6/1998 |
| WO | WO 98/39474 | 9/1998 |
| WO | WO 98/44001 | 10/1998 |
| WO | WO 00/71987 | 11/2000 |
| WO | WO 02/26891 | 4/2002 |
| WO | WO 03/020986 | 3/2003 |
| WO | WO 03/074723 | 9/2003 |
| WO | WO 03/102595 | 12/2003 |
| WO | WO 2004/076653 | 9/2004 |
| WO | WO 2004/087863 | 10/2004 |
| WO | WO 2004/113877 | 12/2004 |
| WO | WO 2005/035725 | 4/2005 |
| WO | WO 2005/044086 | 5/2005 |
| WO | WO 2005/047532 | 5/2005 |
| WO | WO 2005/078121 | 8/2005 |
| WO | WO 2006/018849 | 2/2006 |
| WO | WO 2006/119569 | 11/2006 |
| WO | WO 2006/120434 | 11/2006 |
| WO | WO 2007/027970 | 3/2007 |
| WO | WO 2007/028155 | 3/2007 |
| WO | WO 2007/046108 | 4/2007 |
| WO | WO 2007/081791 | 7/2007 |
| WO | WO 2007/103910 | 9/2007 |
| WO | WO 2007/112281 | 10/2007 |
| WO | WO 2007/147076 | 12/2007 |
| WO | WO 2008/070862 | 6/2008 |
| WO | WO 2008/081451 | 7/2008 |
| WO | WO 2008/098142 | 8/2008 |
| WO | WO 2009/002891 | 12/2008 |
| WO | WO 2009/009769 | 1/2009 |
| WO | WO 2009/030100 | 3/2009 |
| WO | WO 2009/102632 | 8/2009 |
| WO | WO 2009/103110 | 8/2009 |
| WO | WO 2010/085841 | 8/2010 |
| WO | WO 2011/075774 | 6/2011 |

OTHER PUBLICATIONS

Folkersen et al.; "An Immunoprecipitation-Dissociation Technique for Large Scale Antibody Purification and an Antigen Consumption Electroimmunoassay for Antibody Quantitation. A Model Study with Antibodies to Pregnancy Zone Protein"; 1978; Journal of Immunological Methods; 23; pp. 127-135.

Gama-Sosa, M. A., et al. "The 5-methylcytosine content of DNA from human tumors", Nucleic Acids Research, 1983, vol. 11, No. 19, pp. 6883-6894.

Gerlach, "Human lymphocyte antigen molecular typing: how to identify the 1250+ alleles out there," Arch. Pathol. Lab. Med., 2002, vol. 126, pp. 281-284.

Gibson et al., "A Novel Method for Real Time Quantitative RT-PCR," Genome Res., 1996, vol. 6, pp. 995-1001.

Guilbert et al., "Preparation and Functional Characterization of Villous Cytotrophoblasts Free of Syncytial Fragments," Placenta, 2002, vol. 23, Iss. 2-3, pp. 175-183.

Hoffmann et al.; "Continuous Free-Flow Electrophoresis Separation of Cytosolic Proteins from the Human Colon Carcinoma Cell Line LIM 1215: A Non Two-Dimensional Gel Electrophoresis-Based Proteome Analysis Strategy"; 2001; Proteomics; 1; pp. 807-818.

Isaka et al., "Telomerase activity in human trophoblast," Trophoblast Research, 1999, vol. 13, pp. 377-394.

Just et al., "Determination of relative telomere length by flow cytometry," Dako Ltd UK, date unknown, 2 pages.

King et al., "Surface Expression of HLA-C Antigen by Human Extravillous Trophoblast," Placenta, 2000, vol. 21 Iss. 4, pp. 376-387.

Kyo et al., "Expression of Telomerase Activity in Human Chorion," Biochemical and Biophysical Research Communications, 1997, vol. 241, Iss. 2, pp. 498-503.

Li et al., "Detection of Paternally Inherited Fetal Point Mutations for β-Thalassemia Using Size-Fractionated Cell-Free DNA in Maternal Plasma," The Journal of the American Medical Association, 2005, vol. 293, No. 7, pp. 843-849.

Li et al., "Size Separation of Circulatory DNA in Maternal Plasma Permits Ready Detection of Fetal DNA Polymorphisms," Clinical Chemistry, 2004, vol. 50, No. 6, pp. 1002-1011.

Lo, "Fetal DNA in maternal plasma: application to non-invasive blood group genotyping of the fetus," (2001) Transfus. Clin. Biol. 8:306 (Abstract), 1 page.

Middleton et al., "Frequency of HLA-B alleles in a Caucasoid population determined by a two-stage PCR-SSOP typing strategy," Hum. Immunol., 2000, vol. 61(12), pp. 1285-1297 (Abstract), 1 page.

Nelson et al., "Microchimerism and HLA-Compatible Relationships of Pregnancy in Scleroderma", The Lancet, vol. 351, Feb. 21, 1998, pp. 559-562.

Oshop et al., "In ovo delivery of DNA to the avian embryo," Vaccine, 2003, vol. 21, Iss. 11-12, pp. 1275-1281.

Parker et al.; "Biophysical Characteristics of Anti-Galα1-3Gal IgM Binding to Cell Surfaces: Implications for Xenotransplantation," Transplantation, 2001, vol. 71(3), pp. 440-446.

Reed et al., "Non-Invasive Determination of the Paternal HLA Haplotype of a Fetus Using Kinetic PCR to Detect Fetal Microchimerism in Maternal Plasma," Bone Marrow Transplantation, vol. 29, 2002, pp. 527-529.

Schroder, "Transplacental Passage of Blood Cells," Journal of Medical Genetics, 1975, vol. 12, pp. 230-242.

Strijdom et al., "Direct intracellular nitric oxide detection in isolated adult cardiomyocytes: flow cytometric analysis using the fluorescent probe, diaminofluorescein," Journal of Molecular and Cellular Cardiology, 2004, vol. 37, Iss. 4, pp. 897-902.

(56) References Cited

OTHER PUBLICATIONS

Tsang et al., "Optimum dissociating condition for immunoaffinity and preferential isolation of antibodies with high specific activity," Journal of Immunological Methods, vol. 138, 1991, pp. 291-299.
Wang et al., "Cell Separation by Dielectrophoretic Field-flow-fractionation," Analytical Chemistry, 2000, vol. 72, No. 4, pp. 832-839.
Warwick et al., "Detection strategy for maternal antibodies against paternal HPA-1 antigen on fetal platelets," The Lancet, vol. 344, Jul. 2, 1994, p. 64.
"12th Fetal Cell Workshop" Fetal Diagnosis and Therapy, 2001, vol. 16, pp. 437-464.
Adinolfi et al., "Detection of Fetal Cells in Transcervical Samples and Prenatal Diagnosis of Chromosomal Abnormalities," Prenatal Diag., 1995, vol. 15, pp. 943-949.
Adinolfi et al. "Fetal cells in transcervical samples at an early stage of gestation," Journal of Human Genetics, 2001, vol. 46(3), pp. 99-104.
Adinolfi et al., "First trimester prenatal diagnosis using transcervical cells: an evaluation," Hum. Reprod. Update, 1997, vol. 3(4), pp. 383-392.
Adinolfi et al., "Molecular Evidence of Fetal-Derived Chromosome 21 Markers (STRs) in Transcervial Samples," Prenatal Diag., 1995, vol. 15, pp. 35-39.
Albright et al., "Centrifugal separation of cells in sputum specimens from patients with undifferentiated carcinoma," Cytometry, 1986, vol. 7, pp. 536-543.
Al-Mufti et al., "Investigation of Maternal Blood Enriched for Fetal Cells: Role in Screening and Diagnosis of Fetal Trisomies," Am. J. Med. Genet., 1999, vol. 85, pp. 66-75.
Antalis et al., "Isolation of intact nuclei from hematopoietic cell types," Nucl. Acid Res., 1991, vol. 19, p. 4301.
Baerlocher et al., "Telomere Length Measurements in Leukocyte Subsets by Automated Multicolor Flow-Fish," Cytometry Part A, 2003, vol. 55A, pp. 1-6.
Baerlocher et al., "Telomere Length Measurement by Fluorescence In Situ Hybridization and Flow Cytometry: Tips and Pitfalls," Cytometry, 2002, vol. 47, pp. 89-99.
Bauer et al., "Paternity testing after pregnancy termination using laser microdissection of chorionic villi," Int. J. Legal Med., 2002, vol. 116, pp. 39-42.
Bianchi et al., "Direct hybridization to DNA from small numbers of flow-sorted nucleated newborn cells," Cytometry, 1987, vol. 8(2), pp. 197-202, (Abstract) 1 page.
Bianchi, "Fetal Cells in the Mother: From Genetic Diagnosis to Diseases Associated With Fetal Cell Microchimerism," European Journal of Obstetrics & Gynecology and Reproductive Biology, 2000, vol. 92, pp. 103-108.
Bischoff et al., "Cell-free fetal DNA and intact fetal cells in maternal blood circulation: implications for first and second trimester non-invasive prenatal diagnosis," Hum. Reprod., 2002, vol. 8(6), pp. 493-500.
Bischoff et al., "Endocervical fetal trophoblast for prenatal genetic diagnosis," Current Opinion in Obstetrics Gynecology, 2006, vol. 18, pp. 216-220.
Blaschitz et al., "Antibody Reaction Patterns in First Trimester Placenta: Implications for Trophoblast Isolation and Purity Screening," Placenta, 2000, vol. 21, pp. 733-741.
Bohmer, "Fetal Cells from Maternal Blood: Purpose, Biological Questions, Technical Challenges," Intervirology, 1998, vol. 41, pp. 226-231.
Bulmer et al., "Immunohistochemical Characterization of Cells Retrieved by Transcervical Sampling in Early Pregnancy," Prenatal Diag., 1995, vol. 15, pp. 1143-1153.
Busch et al, "Enrichment of fetal cells from maternal blood by high gradient magnetic cell sorting (double MACS) for PCR-based genetic analysis," Prenatal Diagnosis, 1994, vol. 14(12), pp. 1129-1140.
Bussani et al., "Strategies for the isolation and detection of fetal cells in transcervical samples," Prenatal Diag., 2002, vol. 22, pp. 1098-1101.
Bussani et al., "Prenatal Diagnosis of Common Aneuploidies in Transcervical Samples Using Quantitative Fluorescent-PCR Analysis," Mol. Diag. Ther., 2007, vol. 11, pp. 117-121.
Bussani et al., "Use of the Quantitative Fluorescent-PCR Assay in the Study of Fetal DNA from Micromanipulated Transcervical Samples," Mol. Diagn., 2004, vol. 8, pp. 259-263.
Cabuy et al., "Identification of Subpopuations of Cells With Differing Telomere Lengths in mouse and Human Cell Lines by Flow Fish," Cytometry Part A, 2004, vol. 62A, pp. 150-161.
Chui et al., "Non-invasive prenatal diagnosis: On the horizon?" Pharmacogenomics, Ashley Publications, GB, 2003, vol. 4(2), pp. 191-200.
Cioni et al., "Fetal cells in cervical mucus in the first trimester of pregnancy," Prenatal Diag., 2003, vol. 23, pp. 168-171.
Daryani et al., "Detection of Cells of Fetal Origin From Transcervical Irrigations," Prenatal Diagn., 1997, vol. 17(3), pp. 243-248.
De Pauw et al., "Assessment of Telomere Length in Hematopoietic Interphase Cells Using In Situ Hybridization and Digital Fluorescence Microscopy," Cytometry, 1998, vol. 32, pp. 163-169.
Douglas et al., "Isolation of pure villous cytotrophoblast from term human placenta using immnomagnetic microspheres," J. Immunol. Methods, 1989, vol. 119(2), pp. 259-268.
Douglas et al., "Trophoblast in the Circulating Blood During Pregnancy," Am. J.Obstetrics & Gynecology, 1959, vol. 78(5), pp. 960-973.
Fejgin et al., "Fetal cells in the uterine cervix: a source for early non-invasive prenatal diagnosis," Prenatal Diag., 2001, vol. 21, pp. 619-621.
Findlay et al., "Fluorescent polymerase chain reaction: Part I. A new method allowing genetic diagnosis and DNA fingerprinting of single cells," Hum. Reprod. Update, 1996, vol. 2(2), pp. 137-152.
Findlay et al., "Same day diagnosis of Down's syndrome and sex in single cells using multiplex flourescent PCR," J. Clin. Pathol, pp. Mol. Pathol., 1998, vol. 51, pp. 164-167.
Findlay, I. et al., "Using MF-PCR to diagnose multiple defects from single cells: implications for PGD," Mol. Cell. Endocrin., 2001, vol. 183, pp. S5-S12.
Fitzgerald et al., "PCR Amplification of HIV and Cellular DNA Sequences in Formaldehyde-Fixed, Immunoreactive White Blood Cells," BioTechniques, 1993, vol. 15(1), pp. 128-133.
Genbank Accession No. AF047386.
Goldberg et al., "Frist-trimester fetal chromosomal diagnosis using endocervical lavage: A negative evaluation," Am. J. Obstet. Gynecol., 1980, vol. 138, pp. 436-440.
Hahn et al., "Both maternal and fetal cell-free DNA in plasma fluctuate," Ann. NY Acad. Sci., 2001, vol. 945, pp. 141-144 (Abstract) 1 page.
Harkins et al., "Factors Governing the Flow Cytometric Analysis and Sorting of Large Biological Particles," Cytometry, 1987, vol. 8, pp. 60-70.
Harrington et al., "A Mammalian Telomeras-Associated Protein," Science, 1997, vol. 275, pp. 973-977.
Herzenberg et al., "Fetal cells in the blood of pregnant women: detection and enrichment by Fluorescence-activated cell sorting," Proc. Nat'l Acad. Sci. USA, 1979, vol. 76(3), pp. 1453-1455.
Holzgreve et al., "Prenatal Diagnosis using Fetal Cells and Free Fetal DNA in Maternal Blood," Metabolic and Genetic Screening, 2001, vol. 28 (2), pp. 353-362.
Honda et al., "Fetal gender determination in early pregnancy through qualitative and quantitative analysis of fetal DNA I maternal serum," Hum. Genet., 2002, vol. 110(1), pp. 75-79.
Hymer at al., "Isolation of Nuclei from Mammalian Tissues Through the uUse of Triton X-100," J. Histochem Cytochem, 1964, vol. 12, pp. 359-363.
Inglis et al., "Determining blood cell size using microfluidic hydrodynamics," J. Immunol. Methods, 2008, vol. 329, pp. 151-156.
Iverson et al., "Detection and isolation of fetal cells from maternal blood using the fluorescence-activated cell sorter (FACS)," Prenat. Diagn., 1981, vol. 1, pp. 61-73.

(56) References Cited

OTHER PUBLICATIONS

Katz-Jaffe et al., "DNA identification of fetal cells isolated from cervical mucus: potential for early non-invasive prenatal diagnosis," BJOG, 2005, vol. 112, pp. 595-600.
Kingdom et al., "Detection of Trophoblast Cells in Transcervical Samples Collected by Lavage or Cytobrush," Obstet. Gynecol., 1995, vol. 86, pp. 283-288.
Koumantaki et al., "Microsatellite analysis provides efficient confirmation of fetal trophoblast isolation from maternal circulation," Prenat. Diagn., 2001, vol. 21, pp. 566-570.
Krishan et al., "DAPI Fluorescence in Nuclei Isolated from Tumors," J. Histochem Cytochem, 2005, vol. 53, pp. 1033-1036.
Lee et al., "Down syndrome and cell-free fetal DNA in archived maternal serum," Am. J. Obstet. Gynecol., 2002, vol. 187(5), pp. 1217-1221 (Abstract), 1 page.
Lehmann et al., "Real-Time PCR Analysis of DNA and RNA Extracted from Formalin-Fixed and Paraffin-Embedded Biopsies," Methods, 2001, vol. 25, pp. 409-418.
Leitner et al., "Placental alkaline phosphatase expression at the apical and basal plasma membrane in term villous trophoblasts," J. Histochem. Cytochem., 2001, vol. 49(9), pp. 1155-1164.
Leung at al., "Maternal plasma fetal DNA as a marker for preterm labour," Lancet, 1998, vol. 352(9144), pp. 1904-1905.
Lo, "Fetal DNA in Maternal Plasma: Biology and Diagnostic Applications," Clinical Chemistry, 2000, vol. 46(12), pp. 1903-1906.
Lo et al., "Prenatal diagnosis of fetal RhD status by molecular analysis of maternal plasma," N. Engl. J. Med., 1998, vol. 339(24), pp. 1734-1738.
Lo et al., "Quantitative Abnormalities of Fetal DNA in Maternal Serum in Preeclampsia," Clin. Chem., 1999, vol. 45(2), pp. 184-188.
Mantzaris et al., "Preliminary report: correct diagnosis of sex in fetal cells isolated from cervical mucus during early pregnancy," Aus. NZ J. Obstet. Gynecol., 2005, vol. 45, pp. 529-532.
Massari et al., "Non-invasive early prenatal molecular diagnosis using retrieved transcervical trophoblast cells," Hum. Genet., 1996, vol. 97, pp. 150-155.
Michalet et al., "Quantum Dots for Live Cells, in Vivo Imaging, and Diagnostics," Science, 2005, vol. 307, pp. 538-544.
Miller et al., "Transcervical recovery of fetal cells from the lower uterine pole: reliability of recovery and histological/immunocytochemical analysis of recovered cell populations," Hum. Reprod., 1999, vol. 14(2), pp. 521-531.
Mowbray et al., "Maternal response to Paternal Trophoblast Antigens", American Journal of Reproductive Immunology, 1997, vol. 37, pp. 421-426.
Murthy et al., "Size-based microfluidic enrichment of neonatal rat cardiac cell populations," Biomed. Microdevices, 2006, vol. 8, pp. 231-237.
Narath et al., "Automatic Telomere Length Measurements in Interphase Nuclei by IQ-FISH," Cytometry Part A, 2005, vol. 68A, pp. 113-120.
Parks et al., "Chapter 10. Fetal Cells from Maternal Blood: Their Selection and Prospects for Use in Prenatal Diagnosis," Methods in Cell Biology, 1982, vol. 26, pp. 277-295.
Pertl et al., "Fetal DNA in maternal plasma: emerging clinical applications," Obstet. Gynecol., 2001, vol. 98(3), pp. 483-490 (Abstract), 1 page.
Poon et al., "Differential DNA Methylation Between Fetus and Mother as a Strategy for Detecting Fetal DNA in Maternal Plasma," Clinical Chemistry, 2002, vol. 48(1), pp. 35-41.
Reed et al., "The alloantibody response of pregnant women and its suppression by soluble HLA antigens and and anti-idiotypic antibodies," J. Reprod. Immunol., 1992, vol. 20, pp. 115-128.
Rhine et al., "Prenatal sex detection with endocervical smears: Successful results utilizing Y-body fluorescence," Am. J. Obstet. Gynecol., 1975, vol. 122, pp. 155-160.
Rhine et al., "A Simple Alternative to Amniocentesis for First Trimester Prenatal Diagnosis," Birth Defects Orig. Article Ser., 1977, vol. 12(3D), pp. 231-247.
Rodeck et al., "Methods for the Transcervical Collection of Fetal Cells During the First Trimester of Pregnancy," Prenatal Diag., 1995, vol. 15, pp. 933-942.
Ruano et al., "Haplotype of multiple polymorphisms resolved by enzymatic amplification of single DNA molecules," Proc. Natl. Acad. Sci USA, 1990, vol. 87, pp. 6296-6300.
Satyanarayana et al., "Telomeres, Telomerase and Cancer. An Endless Search to Target the Ends," Cell Cycle, 2004, vol. 3(9), pp. 1138-1150).
Schaetzlein et al., "Telemere length is reset during early mammalian embryogenesis," Proc. Nat. Acad. Sci., 2004, vol. 101(21), pp. 8034-8038.
Schmid et al., "Simultaneous Flow Cytometrci Analysis of Two Cell Surface Markers, Telomere Length, and DNA Content," Cytometry 49, pp. 96-105 (2002).
Serlachius et al, "The use of transferrin for enrichment of fetal cells from maternal blood." Prenatal Diagnosis, 2000, vol. 20(5), pp. 407-410.
Shettles, "Use of the Y Chromosome in Prenatal Sex Determination," Nature, 1971, vol. 230, pp. 52-53.
Solier et al., "Secretion of pro-apoptotic intron 4-retaining soluble HLA-G1 by human villous trophoblast," Eur. J. Immuno., 2002, vol. 32, pp. 3576-3586.
Tokumasu et al., "Development and application of quantum dots for immunocytochemistry of human erythrocytes," J. Microscopy, 2003, vol. 211(Pt.3), pp. 256-261.
Trulsson et al., "Telomerase activity in surgical specimens and fine-needle aspiration biopsies from hyperplastic and neoplastic human thyroid tissues," Am. J. Surg., 2003, vol. 186, pp. 83-88.
Truneh et al., "Detection of very low receptor numbers on cells by flow cytometry using a sensitive staining method," Cytometry, 1987, vol. 8, pp. 562-567.
Tutschek et al., "Isolation of Fetal Cells from Transcervical Samples by Micromanipulation: Molecular Confirmation of Their Fetal Origin and Diagnosis of Fetal Aneuploidy," Prenatal Diag., 1995, vol. 15, pp. 951-960.
Uitto et al., "Probing the fetal genome: progress in non-invasive prenatal diagnosis," Trends in Molecular Medicine, Elsevier Current Trends, 2003, vol. 9(8), pp. 339-343.
Van Wijk et al., "HLA-G expression in trophoblast cells circulating in maternal peripheral blood circulating during early pregnancy," Am. J. Obste. Gynec., 2001, vol. 184(5), pp. 991-997.
Vaziri et al., "Evidence for a mitotic clock in human hermatopoietic stem cells, pp. Loss of telomeric DNA with age," Proc. Nat. Acad. Sci. USA, 1994, vol. 91, pp. 9857-9860.
Vona et al., "Enrichment, immunomorphological, and genetic characterization of fetal cells circulationg in maternal blood," Am. J. Pathology, Am. Society for Investigative Pathology, US. 2002, vol. 160(1), pp. 51-58.
Wataganara et al., "Maternal serum cell-free fetal DNA levels are increased in cases of trisomy 13 but not tisomy 18," Hum. Genet., 2003, vol. 112, pp. 204-208.
Weetman, "The Immunology of Pregnancy," Thyroid, 1999, vol. 9(7), pp. 643-646.
Wegmann et al., "Allogeneic Placenta is a Paternal Strain Antigen Immunoabsorbent", J. Immunology, 1979, vol. 122 (1), pp. 270-274.
Wu et al., "Microfluidic continuous particle/cell separation via electroosmotic-flow-tuned hydrodynamic spreading," J. Micromech. Microengr., 2007, vol. 17, pp. 1992-1999.
Yamanishi et al., "Enrichment of rare fetal cells from maternal peripheral blood," expert review of Molecular Diagnostics, Future Drugs, London, GB, 2002, vol. 2(4), pp. 303-311.
Yeoh et al., "Detecting fetal cells in maternal circulation," Lancet, 1989, vol. 2(8667), pp. 869-870.
Zhao et al., "Enrichment of fetal cells from maternal blood by magnetic activated cell sorting (MACS) with fetal cell specific antibodies: one-step versus two-step MACS," Congenital Anomalies—Senten IJO, Sayama Osaka, JP, 2002, vol. 42(2), pp. 120-124.

(56) References Cited

OTHER PUBLICATIONS

Zhong et al., "High levels of fetal erythroblasts and fetal extracellular DNA in the peripheral blood of a pregnant woman with idiopathic polyhydramnios: case report," Prenat. Diagn., 2000, vol. 20(10), pp. 838-841 (Abstract), 1 page.
Adams, "Male DNA in female donor apheresis and CD34-enriched products," (2003) Blood 102:3845-3847.
Ariga, "Kinetics of fetal cellular and cell-free DNA in the maternal circulation during and after pregnancy: implications for noninvasive prenatal diagnosis," (2001) Transfusion 41:1524-1530 (Abstract), 2 pages.
Askelund et al., "Trophoblast deportation part I: Review of the evidence demonstrating trophoblast shedding and deportation during human pregnancy," Placenta, 2011, vol. 32, pp. 716-723.
Bianchi et al., "Isolation of fetal DNA from nucleated erythrocytes in maternal blood," (1990) Proc. Natl. Acad. Sci. USA 87: 3279-3283.
Bugert, "Prenatal HLA typing of uncultured amniocytes prior to the collection of related allogeneic cord blood," (2001) Tissue Antigens 58: 103-106 (Abstract), 1 page.
Chua et al., "Trophoblast deportation in pre-eclamptic pregnancy," Br. J. Obstet Gynaecol., 1991, vol. 98(10), pp. 973-979 (Abstract), 1 page.
Chui et al., "Application of fetal DNA in maternal plasma for noninvasive prenatal diagnosis," (2002) Expert Rev. Mol. Diagn. 2:32 (Abstract), 1 page.
Farina et al., "Fetal DNA in maternal plasma as a screening variable for preeclampsia. A preliminary nonparametric analysis of detection rate in low-risk nonsymptomatic patients," (2004) Prenat Diagn 24:83-86.
Hromadnikova et al., "Quantitative analysis of DNA levels in maternal plasma in normal and Down syndrom pregnancies," (2002) BMC Pregnancy and Childbirth 2:4, pp. 1-5.
Johansen et al., "Trophoblast Deportation in Human Pregnancy—its Relevance for Pre-eclampsia," Placenta, 1999, vol. 20, pp. 531-539.
Lambert et al., "From the simple detection of microchimerism in patients with autoimmune diseases to its implication in pathogenesis," (2001) Annals NY Acad. Sci. Volume 945: 165-171. (Abstract), 1 page.
Middleton et al., "A New Allele Frequency Database," Scientific Communications, 2002, available from www.allelefrequencies.net, 2 pages.
Poon et al., "Circulating fetal DNA in maternal plasma," (2001) Clin. Chim. Acta. 313:151 (Abstract), 1 page.
Sekizawa et al., "Prenatal screening of single-gene disorders from maternal blood," (2001) Am. J. Pharmacogenomics 1:111 (Abstract), 1 page.
Torricelli et al., "Isolation of fetal cells from the maternal circulation: prospects for the non-invasive prenatal diagnosis," (2001) Clin Chem Lab Med 39:494 (Abstract), 1 page.
Wachtel et al., "Fetal cells in maternal blood," (2001) Chin Genet 2001: 59: 74-79. (Abstract), 2 pages.
Zhong et al., "Circulating Fetal and Maternal DNA in Pregnancies at Risk and Those Affected by Preeclampsia," (2001) Annals NY Acad. Sci. vol. 945: 138-140.
Ahn et al., "PicoGreen quantitation of DNA: effective evaluation of samples pre- or post-PCR," Nucl. Acid Res., 1996, vol. 24(13), pp. 2623-2625.
Batova et al., "Base specificity and binding of anti-ss/dsDNA monoclonal antibody. Application to the determination of ssDNA," Biochem. Mol. Biol. Int., 1993, vol. 29(3), pp. 451-466.
Berglund et al., "Isolation of viable tumor cells following introduction of labelled antibody to an intracellular oncogene product using electroporation," J. Immun. Methods, 1989, vol. 125, pp. 79-87.
Bossuyt et. al., "Current approaches to histocompatibility testing. A short overview," (1997) Acta. Clin. Belg. 52(2):92-98.
Bunce et al., "Molecular HLA typing—the brave new world," Transplantation, 1997, vol. 64(11), pp. 1505-1513.
Chen et al., "New aspects in Histocompatibility Testing," (1996) Laboratory Medicine Newsletter Mar. vol. 4, No. 3.
Coppola et al.; "High-Performance Liquid Chromatography of Amino Acids, Peptides and Proteins: XCI liB . Comparison of Methods for the Purification of Mouse Monoclonal Immunoglobulin M Autoantibodies"; 1989; Journal of Chromatography; 476; pp. 269-290.
Cuatrecasas, "Protein Purification by Affinity Chromatography," J. Bio. Chem., 1970, vol. 245, p. 3059.
Doxiadis et al., "The short story of HLA and its methods," (2003) Dev. Ophthalmol. 36:5 (Abstract), 1 page.
King et al., "Evidence for the Expression of HLA-C Class I mRNA and Protein by Human First Trimester Trophoblast," J. Immunol., 1996, vol. 156, pp. 2068-2076.
Koskimies et. al., "MHC genes and histocompatibility. A review," (1997) Ann. Chir. Gynaecol. 86(2):171-179.
Little et al., "Current methodologies of human leukocyte antigen typing utilized for bone marrow donor selection," (1998) Curr. Opin. Hematol. 5:419 (Abstract), 1 page.
Lo et al., "Presence of fetal DNA in maternal plasma and serum," Lancet, 1997, vol. 350(9076), pp. 485-487.
Marsh et al., "Nomenclature for factors of the HLA system, 2002," Tissue Antigens, 2002, vol. 60(5), pp. 407-464.
Matthews et al., "Telomerase activity and telomere length in thyroid neoplasia: biological and clinical implications," J. Pathol., 2001, vol. 194, pp. 183-193.
Middleton, "Current and Emerging Technology for HLA Typing," (2002) Int. J. Hematol. 76 Suppl 2:150-1.
Mytilineos, "HLA testing: the state of the art of genomic methods in 1996," (1996) Nephrol Dial. Transplant 11:2129-2134.
Nevens et al.; "Affinity Chromatographic Purification of Immunoglobulin M Antibodies Utilizing Immobilized Mannan Binding Protein"; 1992; Journal of Chromatography; 597; pp. 247-256.
Ni et al., "Prenatal determination of a variable number of tandem repeats in intron 40 of the von Willebrand factor gene from maternal peripheral blood using the polymerase chain reaction," Human Heredity, 2000, vol. 50, No. 3, pp. 201-204.
Pile, "Broadsheet No. 51: HLA and disease associations," (1999) Pathology 31:202-212.
Ray et al., "LifeMatch: A Microsphere Based Methodology for HLA DNA-Based Typing and Antibody Screening," Euro. Fed. for Immunogenetics, Jun. 2001, Issue 33, pp. 13-14.
Robinson et al., "IMGT/HLA and IMGT/MHC: sequence databases for the study of major histocompatibility complex," Nucl. Acid. Res., 2003, vol. 31(1), pp. 311-314.
Robinson et al., "IMGT/HLA Database—a sequence database for the human major histocompatibility complex," (2000) Tissue Antigens 55: 280-287.
Rouger et. al., "Advances in the use of monoclonal antibodies for blood group testing," (1997) Transfus. Clin. Biol. 4:345 (Abstract), 1 page.
Seimiya et al., "Involvement of 14-3-3 proteins in nuclear localization of telomerase," EMBO J., 2000, vol. 19(11), pp. 2652-2661.
Seki et al., "Diagnosis of Pancreatic Adenocarcinoma by Detection of Human Telomerase Reverse Transcriptase Messenger RNA in Pancreatic Juice with Sample Qualification," Clin. Cancer Res., 2001, vol. 7, pp. 1976-1981.
Shorter et al., "Antigenic Heterogeneity of Human Cytotrophoblast and Evidence for the Transietn Expression of MHC Class I Antigens Distinct from HLA-G," Placenta, 1993, vol. 14, pp. 571-582.
Sidransky, "Emerging Molecular Markers of Cancer," Nature Reviews, 2002, vol. 2, pp. 210-219.
Sisson et al., "An Improved Method for immobilizing IgG antibodies on protein A-agarose," Journal of Immunological Methods, 1990, vol. 127, pp. 215-220.
Szekeres-Bartho et al., "Immunological relationship between the mother and the fetus", Intern. Rev. Immunol., Nov.-Dec. 2002, vol. 21, pp. 471-495.
Warren et al., "Prenatal Sex Determination from Exfoliated Cells Found in Cervical Mucosa," Am. J. Hum. Genet., 1972, vol. 24, p. 29a.
Williams et al., "Molecular diversity of the HLA-C gene identified in a caucasian population," Hum. Immunol., 2002, vol. 63(7), pp. 602-613 (Absract).

(56) References Cited

OTHER PUBLICATIONS

Zachary et al., "Strategies for determining HLA compatibility in related donor bone marrow transplantation," (1997) Transplantation 64:828-835. (Abstract), 2 pages.

Zou et al., "Random priming PCR strategy to amplify and clone trace amounts of DNA," BioTechniques, 2003, vol. 35(4), pp. 758-760, 762-765 (Abstract).

Zheng et al. "Prenatal diagnosis from maternal blood: simultaneous immunophenotyping and FISH of fetal nucleated erythrocytes isolated by negative magnetic cell sorting," Journal of Medical Genetics, Dec. 1993, vol. 30, No. 12, pp. 1051-1056.

International Search Report prepared by the Australian Patent Office on Jun. 1, 2010, for International Application No. PCT/AU2010/000438.

Written Opinion prepared by the Australian Patent Office on Jun. 1, 2010, for International Application No. PCT/AU2010/000438.

Bianchi et al., "Large Amounts of Cell-free Fetal DNA Are Present in Amniotic Fluid," Clinical Chemistry, 2001, vol. 47, No. 10, pp. 1867-1869.

Bird et al., "Non-methylated CpG-rich islands at the human alpha-globin locus: implications for evolution of the alpha-globin pseudogene," The EMBO Journal, 1987, vol. 6, No. 4, pp. 999-1004.

Bird, "CpG-rich islands and the function of DNA methylation," Nature, 1986, vol. 321, No. 6067, pp. 209-213.

Boat et al., "Cystic Fibrosis," The Metabolic Basis of Inherited Disease—6th Edition, Ed. Scriver, McGraw-Hill, 1989, vol. 2, Chapter 108, pp. 2649-2680.

Chiu et al., "Non-invasive prenatal diagnosis: On the horizon?" Pharmacogenomics, Ashley Publications, GB, 2003, vol. 4(2), pp. 191-200.

Davalieva et al., "Non-invasive fetal sex determination using real-time PCR," Journal of Maternal-Fetal and Neonatal Medicine, 2006, vol. 19, No. 6, pp. 337-342.

Du et al., "Rapid separation and laser-induced fluorescence detection of mutated DNA by capillary electrophoresis in a self-coating, low-viscosity polymer matrix," Electrophoresis, 2003, vol. 24, Iss. 18, pp. 3147-3153.

Han et al., "Characterization and Optimization of an Entropic Trap for DNA Separation," Analytical Chemistry, 2002, vol. 74, Iss. 2, pp. 394-401.

Hecker et al., "Analysis and purification of nucleic acids by ion-pair reversed-phase high-performance liquid chromatography", Journal of Biochemical and Biophysical Methods, 2000, vol. 46, Iss. 1-2, pp. 83-93.

Horlitz et al., "Optimized Quantification of Fragmented, Free Circulating DNA in Human Blood Plasma Using a Calibrated Duplex Real-Time PCR," PLoS One, 2009, vol. 4, Iss. 9, e7207.

Lin et al., "Selective extraction of size-fractioned DNA samples in microfabricated electrophoresis devices," Journal of Chromatography A, 2003, vol. 1010, Iss. 2, pp. 255-268.

Lo et al., "Quantitative Analysis of Fetal DNA in Maternal Plasma and Serum: Implications for Noninvasive Prenatal Diagnosis," American Journal of Human Genetics, 1998, vol. 62, Iss. 4, pp. 768-775.

Peter et al., "Cell-free DNA Fragmentation Patterns in Amniotic Fluid Identify Genetic Abnormalities and Changes due to Storage," Diagnostic Molecular Pathology, 2008, vol. 17, No. 3, pp. 185-190.

Raptis et al., "Quantitation and Characterization of Plasma DNA in Normals and Patients with Systemic Lupus Erythematosus," The Journal of Clinical Investigation, 1980, vol. 66, Iss. 6, pp. 1391-1399.

Riordan et al., "Identification of the Cystic Fibrosis Gene: Cloning and Characterization of Complementary DNA" Science, 1989, vol. 245, No. 4922, pp. 1066-1073.

Teeters et al., "Adsorptive membrane chromatography for purification of plasmid DNA," Journal of Chromatography A, 2003, vol. 989, Iss. 1, pp. 165-173.

Xu et al. "Reduced viscosity polymer matrices for microchip electrophoresis of double-stranded DNA," Analyst, 2003, vol. 128, Iss. 6, pp. 589-592.

Zhong et al., "Direct quantification of fetal cells in maternal blood by real-time PCR," Prenatal Diagnosis, 2006, vol. 26, Iss. 9, pp. 850-854.

Geifman-Holtzman et al., "Detection of fetal HLA-DQα sequences in maternal blood: A gender-independent technique of fetal cell identification," Prenatal Diagnosis, 1995, vol. 15, Iss. 3, pp. 261-268.

Pietrapertosa, et al., "Analysis of HLA-DRB1*-A* and -B* alleles in prenatal diagnosis for determination of maternal contamination in fetal DNA," Molecular Human Reproduction, 2002, vol. 8, No. 6, pp. 586-588.

\* cited by examiner

METHODS FOR OBTAINING FETAL GENETIC MATERIAL

CROSS REFERENCE TO RELATED APPLICATIONS

This application is a national stage application under 35 U.S.C. 371 of PCT Application No. PCT/AU2010/00438 having an international filing date of 20 Apr. 2010, which designated the United States, which PCT application claimed the benefit of U.S. Provisional Application No. 61/171,334 filed 21 Apr. 2009, the entire disclosure of each of which are hereby incorporated herein by reference.

FIELD OF THE INVENTION

The present invention relates to a method of enriching fetal nuclei from a sample. Enriched fetal nuclei can be used in a variety of procedures including, detection of a trait of interest such as a disease trait, or a genetic predisposition thereto, gender typing and parentage testing.

BACKGROUND OF THE INVENTION

Early prenatal diagnosis to detect fetal genetic disorders is desirable for both expectant mothers and physicians to make informed decisions. Definitive methods of invasive prenatal testing (amniocentesis and chorionic villous sampling) carry a small, but significant risk of miscarriage, and the results are rarely available before 13 weeks of pregnancy because of the time required for cell culture and analysis.

"Non-invasive" screening with maternal serum analyte screening and ultrasound can identify individuals at risk for fetal aneuploidy (predominantly trisomy 21), but a positive screening result still requires a subsequent invasive procedure for a definitive diagnosis. Of some 25-30 such procedures, only one will actually show a fetal aneuploidy.

Many laboratories around the world have been attempting for over a decade to develop non-invasive (i.e. venupuncture only) methods to isolate and analyse fetal cells. An obvious advantage is that definitive results can be obtained using molecular techniques such as fluorescence in-situ hybridization (FISH) and quantitative fluorescent polymerase chain reaction (QF-PCR) on recovered fetal cells.

The presence of fetal cells in maternal blood provides potentially the best possible source of cells for non-invasive prenatal diagnosis. However fetal cells are present at very low numbers, and their isolation is not a trivial task, with only 1 or 2 fetal cells being present per 10 ml maternal blood. Evidence also indicates that the presence of intact fetal cells in the maternal circulation is not a universal event.

An alternative to peripheral blood sampling is the isolation and analysis of trophoblasts from transcervical samples. Unlike maternal blood in which multiple circulating fetal cell types exist, fetal cells in the transcervical samples are all of placental origin and are overwhelmingly trophoblasts (Bischoff and Simpson, 2006).

It was long assumed that the cervical canal contained trophoblasts of fetal origin. The early embryo is covered with chorion levae, but later in the gestation the chorionic surface is smooth. However, it was not until 1971 that the presence of fetal cells in the endocervix was confirmed by identification of Y-chromosome bearing cells in midcervical mucous samples collected with a cotton swab (Shettles et al., 1971). Subsequent reports assumed that these fetal cells were shed from the regressing chorionic villous into the lower uterine pole (Warren et al., 1972, Adinolphi et al., 1995, Rhine et al., 1975). In this scenario, it is most likely to occur between 7 and 13 weeks gestation, before fusion of the deciduas basalis and parietalis. Desquamated trophoblasts are believed first to accumulate behind the cervical mucous at the level of the internal opening section (Bulmer et al., 1995, Adinolphi and Sherlock, 1997) and then become ensconced in the cervical mucous.

These biologic events thus define the window of opportunity for endocervical sampling to be of use for prenatal diagnoses, although several studies have demonstrated trophoblast recovery as early as 5 weeks gestation (Katz-Jaffe et al., 2005, Mantzaris et al., 2005).

Efforts to extract trophoblasts were first made in the 1970's. Rhine et al. (1975 and 1977) described "antenatal cell extractors" that flush the endocervical canal with sterile saline to recover fetal cells. After culture, fetal metaphases from recovered cells were detected in approximately 50% of cases. However, other investigators reported negative results (Goldberg et al., 1980), leading to overall skepticism concerning clinical application.

Interest was rekindled in the 1990's following the introduction of chorion villus sampling (CVS). Transcervical specimens were collected by cotton swabs, cytobrush, aspiration of cervical mucus with a catheter, lavage of the endocervical canal or uterine. A variety of techniques resulted in detection of fetal cells in 40-90% of specimens examined (Adinolfi et al., 1995a, Bussani et al., 2002, Cioni et al., 2003, Fejgin et al., 2001, Massari et al., 1996; Miller et al., 1999; Rodeck et al., 1995; Tuttschek et al., 1995). Again, however, interest waned in most centres because analysis was difficult. The presumptive fetal cells embedded in mucous were not readily amenable to FISH. More recently, molecular PCR techniques for micromanipulated cell clumps of trophoblastic origin were demonstrated to have utility for transcervical samples (Bussani et al., 2004; Bussani et al., 2007; Katz-Jaffe et al., 2005).

Most transcervical specimens contain a variety of maternally derived cells (leukocytes, macrophages, squamous epithelia, columnar epithelia, and endocervical cells) as well as different fetal-derived cells (cytotrophoblasts and syncytiotrophoblasts) (Bulmer et al., 1995, Miller et al., 1999). The frequency of each fetal cell type is variable and seemingly dependent on the collection method and gestational age.

The literature is inconsistent with regard to the number and relative proportion of fetal cells which can be recovered in transcervical specimens. Kingdom et al. (1995) reported the frequency of fetal XY cells recovered endocervical lavage to range from 2 to 8%. In the same study, FISH results using a cytological brush ranged from 1 to 5% of total cells. Daryani et al. (1997) reported fetal cells to be 3.6 to 47.8% of total cells, based on 3-31 fetal cells obtained by aspiration. Katz-Jaffe et al. (2005) claimed a higher absolute number of fetal cells, up to 250 cells/ml of dissociated mucous, based on immunohistochemistry staining with trophoblast specific monoclonal antibodies (NDOG1 and FT141.1).

Nuclei have previously been isolated from cells and tissues, usually by detergent treatment, or enforced lysis of cells by ammonium chloride to liberate nuclei from intact cells (for example see, Hymer and Cuff 1963; Antalis and Godbolt 1991; Krishan and Dandekar 2005). U.S. Pat. No. 5,447,864 discloses a method for isolating cell nuclei via selective lysis of the cell plasma membranes leaving the majority of nuclear membranes intact. U.S. Pat. No. 4,906,561 discloses a method for isolating cell nuclei by detergent lysis with simultaneous fluorescent labelling of nuclei for subsequent cytometric analysis. EP 0944829 and WO 98/026284 disclose a method for selectively lysing fetal nucleated red blood cells within a blood sample obtained from pregnant women by saponin mediated cell lysis.

There is a need for alternate methods of enriching fetal genetic material from a pregnant female.

SUMMARY OF THE INVENTION

The present inventors have surprisingly found that free fetal nuclei are present in samples obtained from a pregnant female. Thus, in a first aspect the present invention provides a method of enriching fetal nuclei, the method comprising selecting fetal nuclei from a sample from a pregnant female.

Whilst fetal nuclei had previously been isolated, this was in the context of first obtaining intact cells, followed by disrupting the cell membranes to liberate the nuclei. Accordingly, in a particularly preferred embodiment, the method of the first aspect does not comprise the step of disrupting the cell membrane of cells in the sample, for example by using a detergent or other chemical agent. In other words, the method can be considered as a method of enriching free fetal nuclei from the sample.

In one embodiment, the method comprises selecting fetal nuclei based on their size. For example, in an embodiment the method comprises selecting cellular material which is less than about 10 µm, more preferably less than about 8 µm, in size.

In a further embodiment, the method comprises selecting cellular material which is between about 5 µm and about 7 µm in size. In a further embodiment, the method comprises selecting cellular material which is about 6 µm in size.

In a further embodiment, the cellular material is selected using: a cell strainer, flow cytometry, microfluidics, or a combination thereof.

In an alternate embodiment to enrichment based on size, the method comprises selecting fetal nuclei using an agent which binds said nuclei. Examples of types of molecules which can be bound by an agent and be used to enrich fetal nuclei include, but are not limited to, Nuclear Membrane Proteins, Nuclear Lamins, and Nuclear Pore Proteins, or a combination thereof. In an embodiment, the agent binds a molecule selected from: Nuclear Membrane Protein, Lamin A, Lamin B, Lamin C, Glial Cell Missing 1 (GCM1), Eomesodermin homolog protein (EOMES), Nucleoporin P62, and Nuclear Envelope GP210, or a combination thereof. The molecules may further include trophoblast specific transcription factors expressed by the fetal cells. Examples of such transcription factors may include, but are not limited, to HoxB6, HoxC5, HoxC6, Hox3F, HB24, GAX, MSX2, DLX4, Pit-1, AP-2n, TEF-1, TEF-3, and Ets-1, or a combination thereof.

In a preferred embodiment, the agent binds Nuclear Membrane Protein or MSX2 (Hox8).

In a preferred embodiment, the agent is an antibody or antibody fragment.

In an embodiment, the agent is bound to a detectable label or isolatable label.

In an alternate embodiment, the method further comprises binding to the agent a detectable label or isolatable label.

Examples of suitable labels include, but are not limited to, a fluorescent label, a radioactive label, a paramagnetic particle, a chemiluminescent label, a label that is detectable by virtue of a secondary enzymatic reaction, and a label that is detectable by virtue of binding to a molecule.

In an embodiment, the step of selecting fetal nuclei comprises detecting the label and selecting the labelled nuclei.

In one embodiment, the detectable label or isolatable label is a fluorescent label and the step of selecting the fetal nuclei comprises performing fluorescence activated cell sorting.

In another embodiment, the detectable label or isolatable label is a paramagnetic particle and the step of selecting the fetal nuclei comprises exposing the labelled nuclei to a magnetic field.

In a further embodiment, the sample is at least partially mechanically and/or enzymatically disaggregated before the fetal nuclei are selected.

Preferably, the at least partially mechanically disaggregating the sample comprises gentle pipetting using an about 1 ml pipette and/or using forceps.

Preferably, the at least partially enzymatically disaggregating the sample comprises contacting the sample with a collagenase, a protease or a combination thereof.

In yet another embodiment, the method comprises selecting cellular material which is less than about 10 µm and positively selecting fetal nuclei using an agent which binds said nuclei.

To increase the quantity of fetal DNA obtained, the method of the invention may also comprises selecting fetal cells. Fetal cells can be enriched using any method known in the art including, but not limited to, positive selection using an agent which binds fetal cells but not maternal cells, and/or negative selection using an agent which binds maternal cells but not fetal cells. In an embodiment, the method comprises combining the fetal nuclei and fetal cells.

In a preferred embodiment, the fetal cells are multinucleated fetal cells. More preferably, the multinucleated fetal cells are syncytiotrophoblasts.

In one embodiment, the method comprises
i) at least partially mechanically disaggregating the sample to produce a cellular material suspension,
ii) filtering the suspension through a first cell strainer which has a mesh size of at least about 100 µm and collecting the cellular material that passed through the first cell strainer,
iii) filtering the cellular material collected in step ii) through a second cell strainer which has a mesh size of less than about 40 µm and collecting the cellular material that did not pass through the second cell strainer, and independently collecting the cellular material that passed through the second cell strainer,
iv) filtering the cellular material collected in step iii), which passed through the second cell strainer, through a third cell strainer which has a mesh size of less than about 10 µm and collecting the cellular material that passed through the third cell strainer, and
v) combining the cellular material obtained from step iii), which did not pass through the cell second cell strainer, which comprises fetal cells with the cellular material obtained from step iv) which comprises fetal nuclei.

In an alternate embodiment, the method comprises
i) at least partially enzymatically disaggregating the sample to produce a cellular material suspension,
ii) filtering the suspension through a first cell strainer which has a mesh size of less than about 40 µm and collecting the cellular material that did not pass through the first cell strainer, and independently collecting the cellular material that passed through the first cell strainer,
iii) filtering the cellular material collected in step ii), which passed through the first cell strainer, through a second cell strainer which has a mesh size of less than about 10 μm and collecting the cellular material that passed through the second cell strainer, and iv) combining the cellular material obtained from step ii), which did not pass through the first cell strainer, which comprises fetal cells with the cellular material obtained from step iii) which comprises fetal nuclei.

In yet another embodiment, the method comprises i) at least partially mechanically disaggregating the sample to produce a cellular material suspension, ii) filtering the suspension through a cell strainer which has a mesh size of at least about 100 μm and collecting the cellular material that passed through the cell strainer, iii) sorting the cellular material collected in step ii) by fluorescent activated cell separation (FACS) based on forward scatter and collecting cellular material which is at least about 40 μm in size, iv) sorting the cellular material collected in step ii) and/or step iii) by fluorescent activated cell separation (FACS) based on forward scatter and collecting cellular material which is less than about 10 μm, and v) combining the cellular material obtained from step iii) which comprises fetal cells with the cellular material obtained from step iv) which comprises fetal nuclei.

In a further embodiment, the method comprises i) at least partially mechanically and/or enzymatically disaggregating the sample to produce a cellular material suspension, ii) sorting the suspension by fluorescent activated cell separation (FACS) based on forward scatter and collecting cellular material which is between about 40 μm and 100 μm in size, and collecting cellular material which is less than about 10 μm, and iii) combining the cellular material which is between about 40 μm and 100 μm in size which comprises fetal cells, with the cellular material which is less than about 10 μm comprising fetal nuclei.

The sample used in the first aspect of the invention can be obtained from any source which potentially contains fetal nuclei. Examples include, but are not limited to, blood, cervical mucous (transcervical samples) or urine. Preferably, the sample is a transcervical sample. Preferably, the transcervical sample is/was obtained from the endocervical canal.

As indicated above, fetal nuclei have been isolated using chemical lysis procedures. However, these techniques do not preferentially lyse fetal cells. To enhance the amount of fetal nuclei obtained, the present inventors have devised a procedure where fetal cells are selected and fetal nuclei liberated using complement mediated lysis.

Accordingly, in another aspect the present invention provides a method of enriching fetal nuclei from a sample from a pregnant female, the method comprising i) enriching fetal cells from the sample, ii) contacting the fetal cells with an antibody that binds thereto, and iii) inducing complement mediated lysis of the fetal cells bound to the antibody to release the fetal nuclei.

Preferably, the fetal cells are syncytialtrophoblasts and/or cytotrophoblasts.

In a preferred embodiment, steps i) and ii) are conducted concurrently and the antibody is also used for the enrichment of the fetal cells.

Examples of antibodies or fragments thereof which can be used for the above aspect include, but are not limited to, those which bind NDOG1, NDOG2, human chorionic gonadotropin, MCP/cd46 (trophoblast/lymphocyte cross-reactive protein), TPBG (Trophoblast glycoprotein), GCSF receptor, ADFP (Adipose Differentiation Related Protein), Apolipoprotein H, Placental Alkaline Phosphatase, CXCR6 (Chemokine receptor 6), HLA-G, CHL1 (extravillous cytotrophoblast antigen), Cytokeratin 7, Cytokeratin 8, Cytokeratin 18, FAS-Associated Phosphatase-1, Folate Binding Protein, FD0161G, Glucose Transporter GLUT3, H315, H316, HAI-1 (Hepatocyte growth factor activator protein-1) human placental lactogen, Id-1, Id-2, IBSP (Integrin Binding SialoProtein), MCSF-Receptor, MNF116, OKT9, plasminogen activator inhibitor 1, PLP-A (prolactin like proteins A), PLP-A (prolactin like proteins A), PLP-B (prolactin like proteins B), PLP-C (prolactin like proteins C), PLP-D (prolactin like proteins D), PLP-F (prolactin like proteins F), PLP-L (prolactin like proteins L), PLP-M (prolactin like proteins M), PLP-N (prolactin like proteins N), SP-1 (trophoblast specific beta 1 glycoprotein), SSEA (Stage Specific Embryonic Antigen), TA1, TA2, Tfeb, Troma1, Trop1 and Trop2, URO-4 (Adenosine Deaminase Binding Protein (ABP), or a combination of any two or more thereof.

In a further embodiment, the fetal nuclei obtained using complement mediated lysis can be further enriched using the method of the first aspect of the invention.

In a further preferred embodiment of the above aspect, step i) comprises at least partially mechanically disaggregating the sample.

The sample used in the methods of the invention can be obtained from any source known in the art to potentially contain fetal nuclei. Examples include, but are not limited to, blood, cervical mucous or urine. Preferably, the sample is a transcervical sample.

The sample used in the above aspect of the invention can be obtained from any source which is known in the art to potentially contains fetal cells. Examples include, but are not limited to, blood, cervical mucous (transcervical samples) or urine. Preferably, the sample is a transcervical sample.

Preferably, the transcervical sample is/was obtained using a flexible aspiration catheter, uterine lavage, a cytobrush or an endocervical lavage. More preferably, the transcervical sample is/was obtained using a flexible aspiration catheter.

Preferably, the sample is/was obtained within 5 to 18 weeks of pregnancy, more preferably within 5 to 15 weeks of pregnancy, and even more preferably within 5 to 12 weeks of pregnancy.

In an embodiment, the method further comprises obtaining the sample.

Also provided is an enriched population of fetal nuclei obtained by a method of the invention.

Furthermore, provided is a composition comprising fetal nuclei of the invention, and a carrier.

Fetal nuclei enriched using a method of the invention can be used to analyse the genotype of the fetus. Thus, in yet another aspect, the present invention provides a method for analysing the genotype of a fetus at a locus of interest, the method comprising i) obtaining enriched fetal nuclei using a method of the invention, and ii) analysing the genotype of at least one fetal nuclei at a locus of interest.

The genotype of the fetus can be determined using any technique known in the art. Examples include, but are not limited to, karyotyping, hybridization based procedures, and/or amplification based procedures.

The genotype of a fetal nuclei can be analysed for any purpose. Typically, the genotype will be analysed to detect the likelihood that the offspring will possess a trait of interest. Preferably, the fetal nuclei is analysed for a genetic abnormality linked to a disease state, or predisposition thereto. In one embodiment, the genetic abnormality is in the structure and/or number or chromosomes. In another embodiment, the genetic abnormality encodes an abnormal protein. In another embodiment, the genetic abnormality results in decreased or increased expression levels of a gene.

In at least some instances, the enrichment methods of the invention will not result in a pure fetal nuclei population. In other words, some maternal cells and/or maternal nuclei may remain. Thus, in a preferred embodiment the methods of diagnosis (determination, analysis etc) further comprises identifying a nuclei as a fetal nuclei.

The enriched fetal nuclei can be used to determine the sex of the fetus. As a result, in a further aspect, the present invention provides a method of determining the sex of a fetus, the method comprising i) obtaining enriched fetal nuclei using a method of the invention, and ii) analysing at least one fetal nuclei to determine the sex of the fetus.

The analysis of the fetal nuclei to determine the sex of the fetus can be performed using any technique known in the art. For example, Y-chromosome specific probes can be used, and/or the nuclei karyotyped.

The enriched fetal nuclei can also be used to identify the father of the fetus. Accordingly, in a further aspect, the present invention provides a method of determining the father of a fetus, the method comprising i) obtaining enriched fetal nuclei using a method of the invention, ii) determining the genotype of the candidate father at one or more loci, iii) determining the genotype of the fetus at one or more of said loci, and iv) comparing the genotypes of ii) and iii) to determine the probability that the candidate father is the biological father of the fetus.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1: Light microscopy of size fractionated free nuclei obtained following size-selection through 8 um pore-size "Nucleopore" track-etched membrane filter (Whatman).

Figure 2:
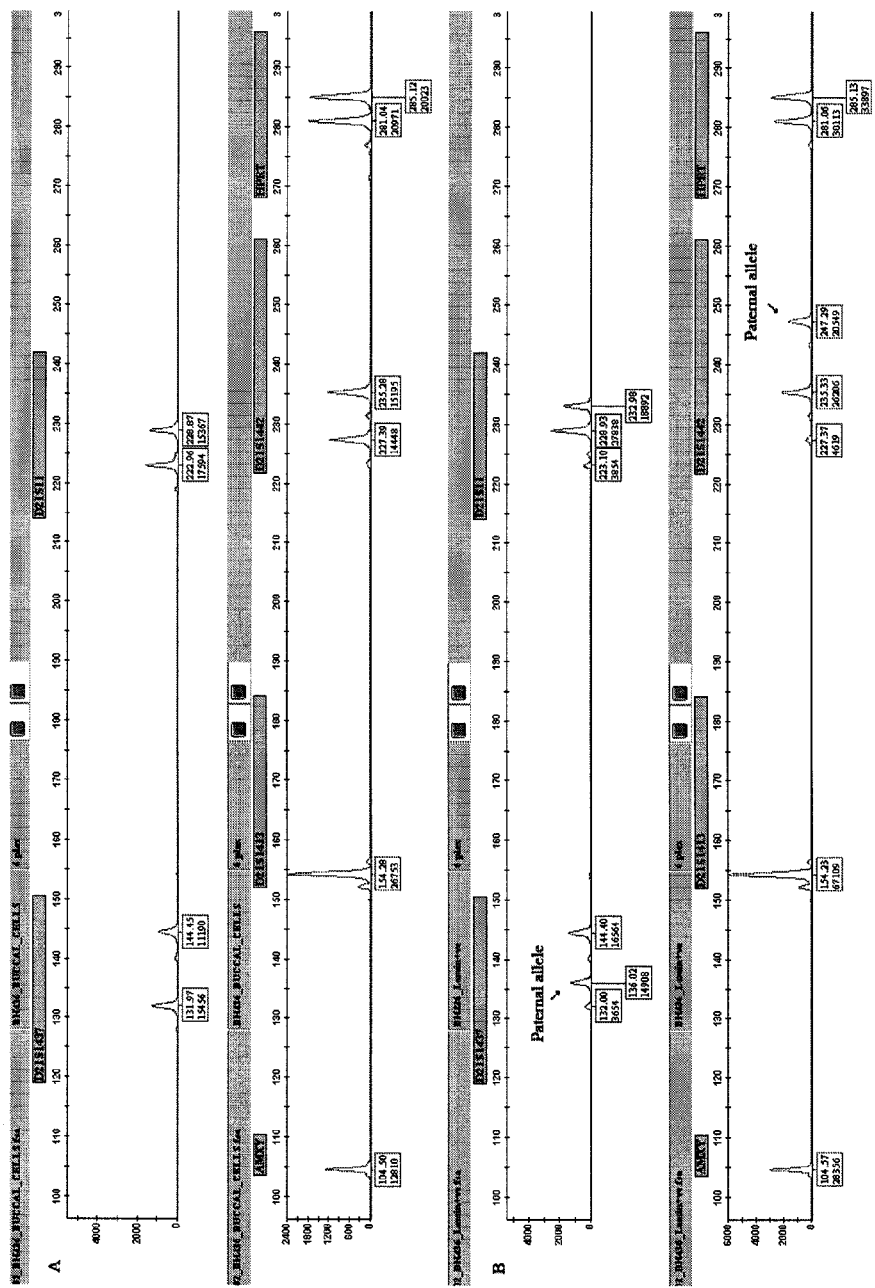

FIG. 2: Electrophoretogram of fluorescent amplified polymerase chain reaction (PCR) products following fetal nuclei selection with chromosome 21 short tandem repeat (STR) markers and the sex markers, amelogenin and polymorphic hypoxanthine guanine phosphoribosyl transferase (HPRT). The x-axis shows the calculated length of the amplified STR amplicons (in base pairs) and the y-axis shows fluorescent intensities in arbitrary units. Comparative analysis of the mother's STR profile (A) with the fetal enriched nuclei STR profile (B) shows paternally inherited alleles confirming the presence of fetal DNA in the sample. The example of fetal nuclei (B) shown is from female fetus exhibiting a mixed DNA profile (maternal+fetal).

Figure 3:
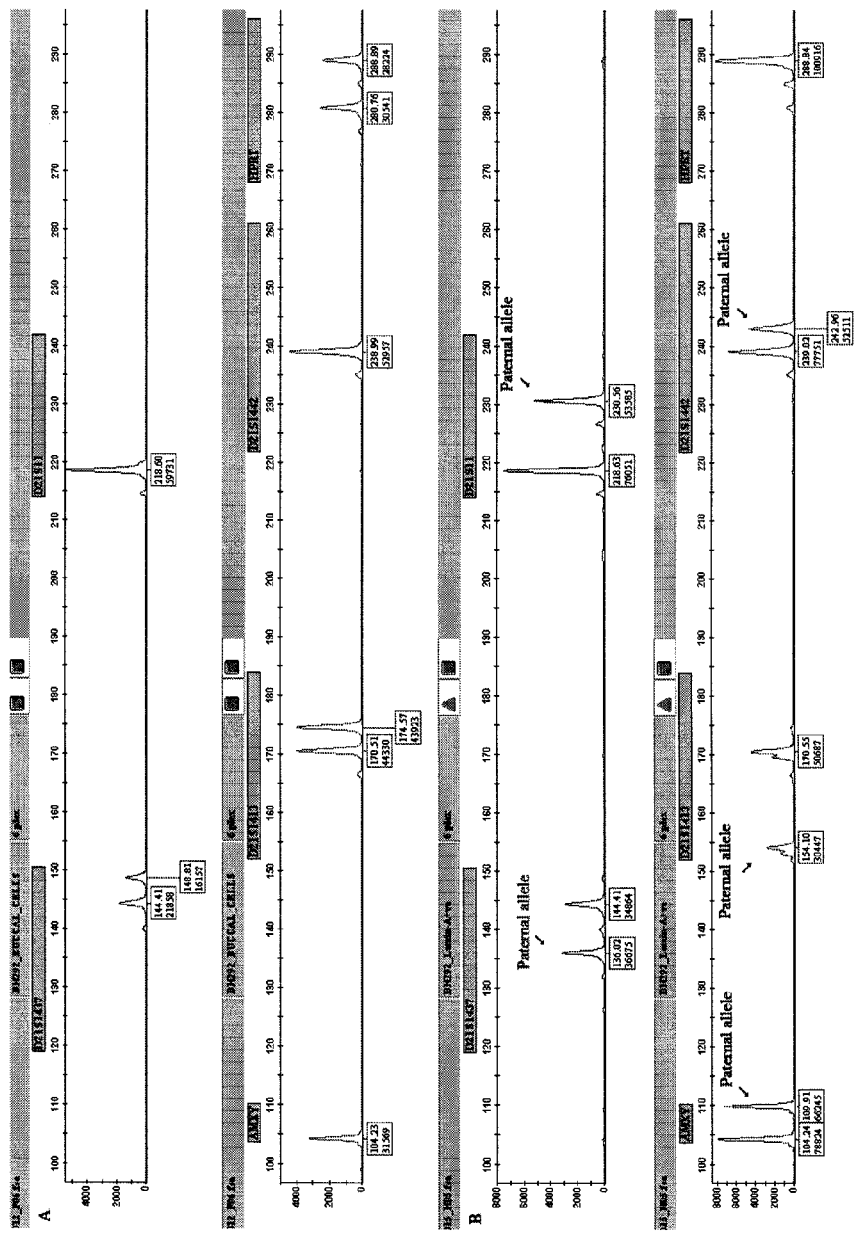

FIG. 3: Electrophoretogram of fluorescent amplified polymerase chain reaction (PCR) products from a pure fetal DNA profile following fetal nuclei selection with chromosome 21 short tandem repeat (STR) markers and the sex markers, amelogenin and polymorphic hypoxanthine guanine phosphoribosyl transferase (HPRT). The x-axis shows the calculated length of the amplified STR amplicons (in base pairs) and the y-axis shows fluorescent intensities in arbitrary units. Comparative analysis of the mother's STR profile (A) with the fetal enriched nuclei STR profile (B) shows paternally inherited alleles confirming fetal origin of isolated fetal nuclei. The example of fetal nuclei (B) shown is from disomic chromosome 21 male fetus.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, fetal cell biology, molecular genetics, immunology, immunohistochemistry, protein chemistry, nucleic acid hybridization, flow cytometry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the terms "enriching" and "enriched" are used in their broadest sense to encompass the isolation of the fetal nuclei such that the relative concentration of fetal nuclei to other cellular material in the treated sample is greater than a comparable untreated sample. Preferably, the enriched fetal nuclei are separated from at least 10%, more preferably at least 20%, more preferably at least 30%, more preferably at least 40%, more preferably at least 50%, more preferably at least 60%, more preferably at least 70%, more preferably at least 75%, more preferably at least 80%, more preferably at least 90%, more preferably at least 95%, and even more preferably at least 99% of the other cellular material in the sample obtained from the pregnant female. Most preferably, the enriched population contains no maternal nuclei or maternal cells (namely, pure). The terms "enrich" and variations thereof are used interchangeably herein with the term "isolate" and variations thereof. Furthermore, a population of nuclei enriched using a method of the invention may only comprise a single fetal nucleous. In addition, the enrichment methods of the invention may be used to isolate a single fetal nucleous.

As used herein, the term "cellular material" refers to cells and portions thereof. In particular, a portion thereof is a cell nuclei. This term may also include clumps of cellular material including cells and/or cell nuclei.

As used herein, the term "free nuclei" refers to nuclei not present within an intact cell in the sample obtained from the pregnant female.

As used herein, the term "nuclei size" and variations thereof refers to the dimensions of the nuclei. Often, the nuclei will be spherical, and hence nuclei size refers to the diameter of the nuclei. However, in some instances at least some of the fetal nuclei may be non-spherical. For non-spherical nuclei, enrichment is based on the smallest diameter of the nuclei, for example, such that they are able to be selected using a cell strainer with a mesh size as defined herein in instances where the nuclei are to pass through the cell strainer.

As used herein, the term "cell size" and variations thereof refers to the dimensions of the cell. Often, fetal cells including multinucleated fetal cells will be spherical, and hence cell size refers to the diameter of the cell. However, in some instances at least some of the cells may be non-spherical. For non-spherical cells, enrichment is based on the smallest diameter of the cell, for example, such that they are able to be selected using a cell strainer with a mesh size as defined herein in instances where the cells are to pass through the cell strainer.

"Syncytiotrophoblasts" are found in the placenta of human embryos. They are the outer syncytial layer of the trophoblasts and actively invade the uterine wall. They form the outermost fetal component of the placenta (also known as 'syntrophoblast') and massively increase the surface area available for nutrient exchange between the mother and the fetus.

"Cytotrophoblasts" form the inner layer of the trophoblasts, interior to the syncytiotrophoblast in an embryo. They serve to anchor the embryonic chorion to the maternal endometrium. Cytotrophoblasts are stem cells in the chorionic villi. During differentiation, mononuclear cytotrophoblast fuse together into the multinucleated syncytiotrophoblasts.

As used herein, the term about, unless stated to the contrary, refers to +/−20%, more preferably +/−10%, more preferably +/−5%, and even more preferably +/−1%, of the designated value.

Sample and Preparation of Nuclei

The term "sample" as used herein includes material taken directly from the female, or material that has already been partially purified or processed. Examples of such partial purification include the removal of at least some non-cellular material, removal of maternal red blood cells, and/or removal of maternal lymphocytes. Examples of samples useful for the invention include, but are not limited to, blood, cervical mucous or urine. Preferably, the sample is a transcervical sample.

As used herein, the term "transcervical sample" refers to material taken directly from the pregnant female comprising cervical mucous. The transcervical sample can be obtained using a variety of sampling methods including, but not limited to, aspiration, irrigation, lavage and cell extraction. The sample may be obtained from sites including, but not limited to, the endocervical canal, external os, internal os, lower uterine pole and uterine cavity. A range of devices are available commercially which may be suitable for obtaining the sample, including but not limited to: "Aspiracath" aspiration catheter (Cook Medical, IN, USA), "Tao" brush endometrial sampler (Cook Medical, IN, USA), Goldstein Sonobiopsy catheter (Cook Medical, IN, USA), Aspiration kit (MedGyn, IL, USA), Endosampler (MedGyn, IL, USA), Endometrial sampler and cervical mucus sampling syringe (Rocket Medical, UK), "Sampling Probet" (Gyněucs Products, Belgium), "Sampling in-out"—endometrial curette (Gynetics Products, Belgium), Endometrial cell sampler (Cheshire Medical Specialities Inc, CT, USA), Aspirette® Endocervical Aspirator and Embryo Transfer Catheter (Cooper Surgical, CT, USA), and Intrauterine Catheter (Cooper Surgical, CT, USA). In an embodiment, the sample is obtained using a device as described in PCT/AU2010/00071.

Once obtained, the sample is preferably stored at 0 to 4° C. until use. The sample is preferably transported and/or stored in HypoThermosol-FRS (HTS-FRS) Medium (Biolife Solutions) at 4° C. For long term storage, the sample is preferably stored in CryoStor CS5 (Biolife Solutions) at −80° C.

In a further embodiment, the sample is transported and/or stored in Gibco™ AmnioMaxII, Gibco™ AmnioMax C-100, or Gibco™ Keratinocyte-SFM supplemented with 2% fetal bovine serum, heparin (2500 U), hydrocortisone (5 µg/ml), insulin (5 µg/ml), human epidermal growth factor (5 µg/ml), human basic fibroblast growth factor (5 µg/ml), 25 µg/ml gentamycin, 50 ng/ml amphotericin B, 1-2 mmol/L vitamin C (ascorbic acid) or a water soluble analogue of vitamin E (1 mmol/L Trolox).

In one embodiment, the transport and/or storage media comprises serum such as bovine calf serum or human serum.

In a further embodiment, the storage medium is degassed with nitrogen to reduce oxidative stress to the samples.

As used herein, the term "at least partially mechanically disaggregating the sample" refers to using non-chemical or non-enzymatic means to disassociate at least some aggregated cells and/or nuclei following removal of the sample from the pregnant female. Typically, but not essential to the invention, this step must not result in the destruction of a significant number of cells or nuclei. Preferably, at least 50%, more preferably at least 60%, more preferably at least 70%, more preferably at least 80%, more preferably at least 90%, more preferably at least 95%, and even more preferably 100% of the cells and/or nuclei in the sample have not been destroyed following this step. Examples of methods for mechanically disaggregating the sample include, but are not limited to, gentle pipetting using an about 1 ml pipette, using forceps, fluid agitation, fluidics movement and/or cutting. Examples of fluid agitation include, but are not limited to, spinning in a vortex, centrifuge or suspension mixer; shaking in a water bath; and stirring using a magnetic stirrer. The fluid agitation should create enough shear force to partially disaggregate the sample. Examples of fluid movement are using pressure or vacuum to disperse cells by passing the fluid through channels/tube/orifice. In a preferred embodiment, mechanically disaggregating the sample comprises gentle pipetting using an about 1 ml pipette and/or using forceps. In one example, the sample it pipetted using a 1 ml pipette until it can easily go up and down the tip.

As used herein, the term "at least partially enzymatically disaggregating the sample" refers to using enzymatic means to disassociate at least some aggregated nuclei and/or cells following removal of the sample from the pregnant female. As the skilled addressee will appreciate, this step must not be result in the destruction of a significant number of cells or nuclei. Preferably, at least 50%, more preferably at least 60%, more preferably at least 70%, more preferably at least 80%, more preferably at least 90%, more preferably at least 95%, and even more preferably 100% of the cells and/or nuclei in the sample have not been destroyed following this step. Examples of enzymes that can be used include, but are not limited to, collagenases, proteases, or a combination thereof.

Proteases (or proteinases) hydrolyze the protein portions of the sample. In one example, an enzyme cocktail, such as pronase which cleaves almost any peptide bond, is used to digest extracellular proteins in a sample. Pronase includes both endo-proteinases and exo-proteinases. Numerous proteolytic compounds that are useful for hydrolyzing proteins are known in the art. Many of these compounds, such as trypsin, chymotrypsin, pepsin, and papain, may be used in addition to or in lieu of promise.

Commercially available mixes of enzymes for treating clumps of cellular material include, but are not limited to, liberase blendzyme which is a combination of collagenase isoform, and thermolysin which can be obtained from Roche.

In another embodiment, the sample is treated with a mucolytic agent. In a preferred embodiment, the sample is treated with the mucolytic agent prior to, or in combination with, at least partially mechanically and/or enzymatically disaggregating the sample. Suitable mucolytic agents may be selected from the group including N-acetyl-L-cysteine and DTT. Preferably, the mucolytic agent is N-acetyl-L-cysteine.

In an embodiment, red blood cells are removed from the sample. Red blood cells can be removed using any technique known in the art. Red blood cells (erythrocytes) may be depleted by, for example, density gradient centrifugation over Percoll, Ficoll, or other suitable gradients. Red blood cells may also be depleted by selective lysis using commercially available lysing solutions (eg, FACSlyse™, Becton Dickinson), Ammonium Chloride based lysing solutions or other osmotic lysing agents.

The methods of the invention can be performed on any pregnant female of any mammalian species. Preferred mammals include, but are not limited to, humans, livestock animals such as sheep, cattle and horses, as well as companion animals such as cats and dogs.

The sample may be obtained at any stage of pregnancy. Preferably the sample is obtained during the first and second trimester of pregnancy. More preferably, the sample is obtained in the first trimester of pregnancy. Ideally the sample is obtained at a stage when a decision can be made for the well-being of the fetus and preferably within a period where an opportunity to make an early decision regarding therapeutic abortion can be made. Preferably, the sample is obtained up to 18 weeks of the pregnancy of a human female.

In a further embodiment, if it is intended to also enrich fetal cells, the sample (which includes any initial processing procedures such as, but not limited to, at least partially mechanically and/or enzymatically disaggregating the sample), or a portion thereof, is examined to determine if multinucleated fetal cells are present. This can be performed using any technique known in the art such as viewing cells in the sample, or portion thereof, under a light microscope.

Maternal cells bound by an antibody can be killed, and thus depleted from a sample, by complement-dependent lysis. For example, antibody labelled cells can be incubated with rabbit complement at 37° C. for 2 hr. Commercial sources for suitable complement systems include Calbiochem, Equitech-Bio and Pel Freez Biologicals. Suitable anti-MHC antibodies for use in complement-dependent lysis are known in the art, for example the W6/32 antibody (AbCam).

Using Nuclei Size to Enrich Fetal Nuclei

Any method known in the art which can be used to enrich nuclei based on nuclei size can be used in the methods of the invention. Examples include, but are not limited to, cell strainers, flow cytometry and/or microfluidics, or a combination thereof.

In one embodiment, the method comprises enriching fetal nuclei using a cell strainer which can be made from, for instance, nylon, metal or etched membrane. For example, a nylon cell strainer(s) with a mesh size of about 10 µm, about 9 µm, about 8 µm, about 7 µm or about 6 µm, can be used such as those sold by Becton Dickinson USA, BD Biosciences, Stem Cell Technologies, Whatman and Miltenyi Biotech.

Preferably, the method comprises selecting nuclei which are between about 6 µm in size.

In flow cytometry, a beam of laser light is projected through a liquid stream that contains nuclei which when struck by the focused light give out signals which are picked up by detectors. These signals are then converted for computer storage and data analysis, and can provide information about various properties. In some embodiments of the present invention, forward scatter data can be used to enrich fetal nuclei based on size. By measuring the light scattered on the side of a nuclei furthest from where the laser hits the nuclei, a measure of nuclei size can be obtained.

Many larger flow cytometers are also "cell sorters", such as fluorescence-activated cell sorters (FACS), and are instruments which have the ability to selectively deposit cellular material from particular populations into tubes, or other collection vessels. In an embodiment, the nuclei are isolated using FACS. This procedure is well known in the art and described by, for example, Melamed, et al. Flow Cytometry and Sorting Wiley-Liss, Inc., New York, N.Y. (1990); Shapiro Practical Flow Cytometry, 4 ed, Wiley-Liss, Hoboken, N.J. (2003); and Robinson et al. Handbook of Flow Cytometry Methods Wiley-Liss, New York, N.Y. (1993); Harkins and Galbraith (1987) and U.S. Pat. No. 4,765,737.

In order to sort nuclei, the instruments electronics interprets the signals collected for each cell or nuclei in the sample as it is interrogated by the laser beam and compares the signal with sorting criteria set on the computer. If the nucleus meets the required criteria, an electrical charge is applied to the liquid stream which is being accurately broken into droplets containing the nucleus. This charge is applied to the stream at the precise moment the nucleus of interest is about to break off from the stream, then removed when the charged droplet has broken from the stream. As the droplets fall, they pass between two metal plates, which are strongly positively or negatively charged. Charged droplets get drawn towards the metal plate of the opposite polarity, and deposited in the collection vessel, or onto a microscope slide, for further examination.

The nuclei can automatically be deposited in collection vessels as single nucleus or as a plurality of nuclei, e.g. using a laser, e.g. an argon laser (488 nm) and for example with a Flow Cytometer fitted with an Autoclone unit (Coulter EPICS Altra, Beckman-Coulter, Miami, Fla., USA). Other examples of suitable FACS machines useful for the methods of the invention include, but are not limited to, MoFlo™ High-speed cell sorter (Dako-Cytomation Ltd), FACS Aria™ (Becton Dickinson), ALTRA™ Hyper sort (Beckman Coulter) and CyFlow™ sorting system (Partec GmbH).

As noted above, microfluidics can also be used to enrich fetal nuclei using the methods of the invention. A microfluidic device can be identified by the fact that it has one or more channels with at least one dimension less than 1 mm.

Common fluids used in microfluidic devices include whole blood samples, bacterial cell suspensions, protein or antibody solutions and various buffers. The use of microfluidic devices to conduct biomedical research and create clinically useful technologies has a number of significant advantages. First, because the volume of fluids within these channels is very small, usually several nanoliters, the amount of reagents and analytes used is quite small. The fabrications techniques used to construct microfluidic devices, discussed in more depth later, are relatively inexpensive and are very amenable both to highly elaborate, multiplexed devices and also to mass production. Furthermore, microfluidic technologies enable the fabrication of highly integrated devices for performing several different functions on the same substrate chip. Examples of the use of microfluidics to enrich cells based on size are described in WO 2004/113877, Murthy et al. (2006), Wu et al. (2007) and Inglis et al. (2008). Considering the present disclosure, the same procedures can readily be adapted by those skilled in microfluidics to enrich fetal nuclei.

In a further embodiment, fetal cells are also enriched using the method of selecting fetal cell based on cell size described in WO 2009/103110. Preferably, this embodiment comprises selecting cells which are between about 30 µm and 150 µm in size, or between about 40 µm and 150 µm in size, or between about 30 µm and 100 µm in size, or between about 40 µm and 100 µm in size, or between about 30 µm and 100 µm in size, or between about 30 µm and 70 µm in size, or between about 40 µm and 70 µm in size. The enriched fetal cells can then be combined with the enriched fetal nuclei.

In an embodiment, a single strainer can be used which comprises three different mesh sizes. For example, the apparatus can comprise a top mesh which has a large pore (mesh) size (for example 100 µm), a middle mesh which has a smaller pore (mesh) size than the top mesh (for example 40 µm), and a bottom mesh which has a smaller pore (mesh) size than the top and middle meshes (for example 8 µm). The cell suspension or sample is placed on the top mesh. Fetal cells are collected (enriched) by selecting the cellular material that passed through the top mesh but did not pass through the middle mesh are collected. Fetal nuclei are collected (enriched) by selecting the cellular material that passed through all three mesh sizes.

In a further example, a single strainer can be used which comprises four different mesh sizes. In addition to the sizes mentioned above, a further mesh between the "top" and "middle" meshes is included (for example 70 µm). In this example, fetal cells are collected (enriched) by selecting the cellular material with a size between 40 µm and 70 µm. Fetal nuclei are collected (enriched) by selecting the cellular material that passed through all four mesh sizes.

Agents which Bind Fetal Nuclei

Fetal nuclei can be positively selected by using agents which bind molecules, typically proteins, which are not significantly produced by maternal cells in the sample and/or which are not present on the cell surface of maternal cells. Typically, molecules used to target fetal nuclei will not be present on the cell surface of fetal cells, however, if there is any "fetal cell contamination" this is not a problem in light of the uses of fetal nuclei as described herein. Examples of types of molecules which can be targeted to enrich fetal nuclei include, but are not limited to, Nuclear Membrane Proteins, Nuclear Lamins, and Nuclear Pore Proteins, or a combination thereof. Examples of specific proteins which can be targeted to enrich fetal nuclei include, but are not limited to, Nuclear Membrane Protein, Lamin A, Lamin B, Lamin C, Glial Cell Missing 1 (GCM1), Eomesodermin homolog protein (EOMES), Nucleoporin P62, and Nuclear Envelope GP210, or a combination thereof. The targeted molecules may further include trophoblast specific transcription factors expressed expressed by the fetal cells. Examples of such transcription factors may include, but are not limited to, HoxB6, HoxC5, HoxC6, Hox3F, HB24, GAX, MSX2, DLX4, Pit-1, AP-2n, TEF-1, TEF-3, and Ets-1, or a combination thereof.

An alternate embodiment, an agent which binds a telomerase or a telomere can be used in the positive selection of fetal nuclei. WO 2006/119569 outlines procedures for selecting fetal cells based on telomerase expression and/or telomere length. As the skilled addressee will appreciate, the procedures described in WO 2006/119569 can readily be adapted to enrich fetal nuclei based on telomerase expression and/or telomere length.

In a further embodiment, fetal cells are also enriched by negative and/or positive selection using an agent. Such methods are known in the art and include procedures described in WO 2009/103110 and/or in WO 2006/119569.

Furthermore, a "cocktail" of agents can be used to select both fetal nuclei and fetal cells. For example, various combinations of antibodies which bind syncitialtrophoblasts, cytotrophoblasts, and free nuclei can be used.

Agents for enriching fetal nuclei can be of any structure or composition as long as they are capable binding, preferably specifically binding, to a target molecule. In one embodiment, the agents useful for the present invention are proteins. Preferably, the protein is an antibody or fragment thereof.

Antibodies or fragments thereof useful for the methods of the invention can be, but are not limited to,
  a monoclonal antibody,
  a polyclonal antibody,
  Fab fragment which contains a monovalent antigen-binding fragment of an antibody molecule that can be produced by digestion of whole antibody with the enzyme papain to yield an intact light chain and a portion of one heavy chain;
  Fab' fragment which can be obtained by treating whole antibody with pepsin, followed by reduction, to yield an intact light chain and a portion of the heavy chain; two Fab' fragments are obtained per antibody molecule;
  (Fab')$_2$ fragment which can be obtained by treating whole antibody with the enzyme pepsin without subsequent reduction; F(ab)2 is a dimer of two Fab' fragments held together by two disulfide bonds;
  Fv, defined as a genetically engineered fragment containing the variable region of the light chain and the variable region of the heavy chain expressed as two chains;
  single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, and tetrabodies etc which may or may not be polyspecific (see, for example, WO 94/07921 and WO 98/44001) and
  single domain antibody, typically a variable heavy domain devoid of a light chain.

Furthermore, the antibodies and fragments thereof may be humanised antibodies, for example as described in EP-A-239400.

Antibodies or fragments thereof useful for the methods of the invention can readily be produced using techniques known in the art. Alternatively, at least some suitable antibodies can be obtained from commercial sources, for example anti-nuclear membrane protein are available from Millipore, whereas anti-lamin A and C monoclonal antibodies are available from AbCam.

The term "specifically binding" refers to the ability of the antibody or fragment thereof to bind with a greater affinity to the target ligand than to other proteins in the sample, more preferably the ability of the antibody or fragment thereof to bind to the target ligand but not other proteins in the sample.

If polyclonal antibodies are desired, a selected mammal (e.g., mouse, rabbit, goat, horse, etc.) is immunised with a suitable immunogenic polypeptide. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art.

Monoclonal antibodies can also be readily produced by one skilled in the art. The general methodology for making monoclonal antibodies by hybridomas is well known Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express single chain antibody (scFv) fragments on the surface of their coat with a large variety of complementarity determining regions (CDRs). This technique is well known in the art.

Preferably, agents used in the methods of the present invention are bound to a detectable label or isolatable label. Alternatively, the agent is not directly labelled but detected using indirect methods such as using a detectably labelled secondary agent (such as a secondary antibody) which specifically binds the agent.

The terms "detectable" and "isolatable" label are generally used herein interchangeably. Some labels useful for the methods of the invention cannot readily be visualized (detectable) but nonetheless can be used to enrich (isolate) fetal nuclei (for example a paramagnetic particle).

Exemplary labels that allow for direct measurement of agent binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such agent (such as antibody)-enzyme conjugates are readily produced by techniques known to those skilled in the art. Further exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like.

Examples of fluorophores which can be used to label agents includes, but are not limited to, Fluorescein Isothiocyanate (FITC), Tetramethyl Rhodamine Isothiocyanate (TRITC), R-Phycoerythrin (R-PE), Alexa™, Dyes, Pacific Blue™ Allophycocyanin (APC), and PerCP™.

The label may also be a quantum dot. In the context of antibody labelling they are used in exactly the same way as fluorescent dyes. Quantum Dots are developed and marketed by several companies, including, Quantum Dot Corporation (USA) and Evident Technologies (USA). Examples of antibodies labelled with quantum dots are described in Michalet et al. (2005) and Tokumasu and Dvorak (2003).

As noted above, in some embodiments the agent is not directly labelled. In this instance, nuclei are identified using another factor, typically a detectably labelled secondary antibody. The use of detectably labelled secondary antibodies in methods of detecting a marker of interest are well known in the art. For example, if an antibody was produced from a rabbit, the secondary antibody could be an anti-rabbit antibody produced from a mouse.

Labelled Fetal Nuclei Detection and Isolation

Fetal nuclei can be selected using a variety of techniques well known in the art, including cell sorting, especially fluorescence-activated cell sorting (FACS), by using an affinity reagent bound to a substrate (e.g., a plastic surface, as in panning), or by using an affinity reagent bound to a solid phase particle which can be isolated on the basis of the properties of the solid phase particles for example beads (e.g., coloured latex beads or magnetic particles). Naturally, the procedure used will depend on how the cells have been labelled.

For selection of nuclei by sorting, the nuclei are labelled directly or indirectly with a substance which can be detected by a cell sorter, preferably a dye. Preferably, the dye is a fluorescent dye. A large number of different dyes are known in the art, including fluorescein, rhodamine, Texas red, phycoerythrin, and the like. Any detectable substance which has the appropriate characteristics for the cell sorter may be used (e.g., in the case of a fluorescent dye, a dye which can be excited by the sorter's light source, and an emission spectra which can be detected by the cell sorter's detectors).

Details of flow cytometry which can be used to select labelled fetal nuclei are described above.

For the selection of nuclei from a sample using solid-phase particles, any particle with the desired properties may be utilized. For example, large particles (e.g., greater than about 90-100 μm in diameter) may be used to facilitate sedimentation. Preferably, the particles are "magnetic particles" (i.e., particles which can be collected using a magnetic field). Typically, nuclei labelled with the magnetic probe are passed through a column, held within a magnetic field. Labelled nuclei are retained in the column (held by the magnetic field), whilst unlabelled cellular material pass straight through and are eluted at the other end. Magnetic particles are now commonly available from a variety of manufacturers including Dynal Biotech (Oslo, Norway) and Miltenyi Biotech GmbH (Germany). An example of magnetic cell sorting (MACS) is provided by Al-Multi et al. (1999) and U.S. Pat. No. 4,675,286.

Laser-capture microdissection can also be used to select labelled nuclei. Methods of using laser-capture microdissection are known in the art (see, for example, U.S. 20030227611 and Bauer et al., 2002).

As the skilled person will appreciate, maternal cells can be labelled with one type of label, and fetal nuclei with another type of label, and the respective cellular material selected on the basis of the different labelling. For example, maternal cells can be labelled as described herein such that they produce a fluorescent green signal, and fetal nuclei can be labelled as described herein such that they produce a fluorescent red signal.

For flow cytometric sorting or microfluidic sorting, nuclei may further be labelled with a DNA-specific fluorescent probe, for example Hoechst 33258, Hoechst 33342, DRAQ-5, etc.

Enrichment and Complement Lysis of Fetal Cells

Fetal cells can be enriched using any method known in the art. In a preferred embodiment, they are enriched by contacting the cells with an agent, preferably, an antibody or fragment thereof, which binds fetal cells. In an embodiment, the agent is detectably labelled.

In an alternate embodiment, and as indicated above, multinucleated fetal cells can be enriched based on cell size.

Preferably, the fetal cells are syncytialtrophoblasts and/or cytotrophoblasts. Examples of antibodies which can be used to enrich syncytialtrophoblasts and/or cytotrophoblasts include, but are not limited to, those which bind NDOG1, NDOG2, human chorionic gonadotropin, MCP/cd46 (trophoblast/lymphocyte cross-reactive protein), TPBG (Trophoblast glycoprotein), GCSF receptor, ADFP (Adipose Differentiation Related Protein), Apolipoprotein H, Placental Alkaline Phosphatase, CXCR6 (Chemokine receptor 6), HLA-G, CHL1 (extravillous cytotrophoblast antigen), Cytokeratin 7, Cytokeratin 8, Cytokeratin 18, FAS-Associated Phosphatase-1, Folate Binding Protein, FD0161G, Glucose Transporter GLUT3, H315, H316, HAI-1 (Hepatocyte growth factor activator protein-1) human placental lactogen, Id-1, Id-2, IBSP (Integrin Binding SialoProtein), MCSF-Receptor, MNF116, OKT9, plasminogen activator inhibitor 1, PLP-A (prolactin like proteins A), PLP-A (prolactin like proteins A), PLP-B (prolactin like proteins B), PLP-C (prolactin like proteins C), PLP-D (prolactin like proteins D), PLP-F (prolactin like proteins F), PLP-L (prolactin like proteins L), PLP-M (prolactin like proteins M), PLP-N (prolactin like proteins N), SP-1 (trophoblast specific beta 1 glycoprotein), SSEA (Stage Specific Embryonic Antigen), TA1, TA2, Tfeb, Troma1, Trop1 and Trop2, URO-4 (Adenosine Deaminase Binding Protein (ABP), or a combination of any two or more thereof.

In a particularly preferred embodiment, the fetal cells are enriched using an agent which binds syncytiotrophoblasts such as a monoclonal antibody which binds NDOG1.

In a further preferred embodiment, the fetal cells are enriched using combinations of agents which bind to villous syncytiotrophoblasts, villous cytotrophoblasts and extra villous cytotrophoblasts. For example, the combination of agents may include an agent which binds NDOG1 (Syncytiotrophoblasts), an agent which binds SP-1 (Villous Cytotrophoblasts and villous syncytiotrophoblasts), and an agent which binds HLA-G (ExtraVillous Cytotrophoblasts).

Complement dependent cytotoxicity (CDC) is initiated upon binding of the C1q subcomponent of C1 to the Fc fragment of an immunoglobulin (Ig), as part of an antigen-antibody (Ab) complex. This binding leads to proteolytic cleavage of the C1r and the C1s subcomponents that renders C1s capable of proteolytically activating the next components, C4 and C2. This leads to the formation of a C3 convertase, which catalyzes the proteolytic cleavage of the third component of complement, C3, into C3a and C3b which, in turn, will transform the C3 convertase into a functional C3/C5 cleaving enzyme. Activation of the complement cascade is completed with cleavage of the C5 component, leading to the assembly of the late-acting components, C5b, C6, C7, C8 and C9, into a terminal complement complex. When assembly of this complex occurs on the cell membrane, a membrane attack complex is generated, thus promoting cell lysis.

To activate the complement cascade, it is necessary for C1q to bind to at least two molecules of IgG1, IgG2, or IgG3 (the consensus is that IgG4 does not activate complement), but only one molecule of IgM, attached to the antigenic target.

Antibody and complement treatment can be used for the negative selection of fetal cells or fetal nuclei in a sample from a pregnant female. Complement mediated cell selection requires a two step incubation of the sample, first with antibody, then with complement.

Lysis of target maternal cells sensitized with a complement fixing antibody can be achieved by, for example, the addition of serum complement which is readily obtainable (and is commercially available from for example, QUIDEL).

Uses

Enriched fetal nuclei comprise the same genetic DNA make up of the somatic nuclei of the fetus, and hence fetal nuclei isolated using the methods of the invention can be analysed for traits of interest and/or abnormalities of the fetus using techniques known in the art. Such analysis can be performed on any cellular material that enables the trait, or predisposition thereto, to be detected. Preferably, this material is nuclear DNA, however, at least in some instances it may be informative to analyse RNA or protein from the isolated fetal nuclei. Furthermore, the DNA may encode a gene, or may encode a functional RNA which is not translated, or the DNA analysed may even be an informative non-transcribed sequence or marker.

In one preferred embodiment, chromosomal abnormalities are detected. By "chromosomal abnormality" we include any gross abnormality in a chromosome or the number of chromosomes. For example, this includes detecting trisomy in chromosome 21 which is indicative of Down's syndrome, trisomy 18, trisomy 13, sex chromosomal abnormalities such as Klinefelter syndrome (47, XXY), XYY or Turner's syndrome, chromosome translocations and deletions, a small proportion of Down's syndrome patients have translocation and chromosomal deletion syndromes which include Pradar-Willi syndrome and Angelman syndrome, both of which involve deletions of part of chromosome 15, and the detection of mutations (such as deletions, insertions, transitions, transversions and other mutations) in individual genes. Other types of chromosomal problems also exist such as Fragile X syndrome, hemophilia, spinal muscular dystrophy, myotonic dystrophy, Menkes disease and neurofibromatosis, which can be detected by DNA analysis.

The phrase "genetic abnormality" also refers to a single nucleotide substitution, deletion, insertion, micro-deletion, micro-insertion, short deletion, short insertion, multinucleotide substitution, and abnormal DNA methylation and loss of imprint (LOI). Such a genetic abnormality can be related to an inherited genetic disease such as a single-gene disorder (e.g., cystic fibrosis, Canavan, Tay-Sachs disease, Gaucher disease, Familial Dysautonomia, Niemann-Pick disease, Fanconi anemia, Ataxia telengectasia, Bloom syndrome, Familial Mediterranean fever (FMF), X-linked spondyloepiphyseal dysplasia tarda, factor XI), an imprinting disorder [e.g., Angelman Syndrome, Prader-Willi Syndrome, Beckwith-Wiedemann syndrome, Myoclonus-dystonia syndrome (MDS)], or to predisposition to various diseases (e.g., mutations in the BRCA1 and BRCA2 genes). Other genetic disorders which can be detected by DNA analysis are known such as thalassaemia, Duchenne muscular dystrophy, connexin 26, congenital adrenal hypoplasia, X-linked hydrocephalus, ornithine transcarbamylase deficiency, Huntington's disease, mitochondrial disorder, mucopolysaccharidosis I or IV, Norrie's disease, Rett syndrome, Smith-Lemli Optiz syndrome, 21-hydroxylase deficiency or holocarboxylase synthetase deficiency, diastrophic dysplasia, galactosialidosis, gangliosidosis, hereditary sensory neuropathy, hypogammaglobulinaemia, hypophosphatasia, Leigh's syndrome, aspartylglucosaminuria, metachromatic leukodystrophy Wilson's disease, steroid sulfatase deficiency, X-linked adrenoleukodystrophy, phosphorylase kinase deficiency (Type VI glycogen storage disease) and debranching enzyme deficiency (Type III glycogen storage disease). These and other genetic diseases are mentioned in The Metabolic and Molecular Basis of Inherited Disease, 8th Edition, Volumes I, II, III and IV, Scriver, C. R. et al. (eds), McGraw Hill, 2001. Clearly, any genetic disease where the gene has been cloned and mutations detected can be analysed.

The methods of the present invention can also be used to determine the sex of the fetus. For example, staining of the isolated fetal nuclei with a Y-chromosome specific marker will indicate that the fetus is male, whereas the lack of staining will indicate that the fetus is female.

In yet another use of the invention, the methods described herein can be used for paternity testing. Where the paternity of a child is disputed, the procedures of the invention enable this issue to be resolved early on during pregnancy. Many procedures have been described for parentage testing which rely on the analysis of suitable polymorphic markers. As used herein, the phrase "polymorphic markers" refers to any nucleic acid change (e.g., substitution, deletion, insertion, inversion), variable number of tandem repeats (VNTR), short tandem repeats (STR), minisatellite variant repeats (MVR) and the like. Typically, parentage testing involves DNA fingerprinting targeting informative repeat regions, or the analysis of highly polymorphic regions of the genome such as HLA loci.

Analysis of Fetal Nuclei

Fetal nuclei enriched/detected using the methods of the invention can be analysed by a variety of procedures, however, typically genetic assays will be performed. Genetic assay methods include the standard techniques of karyotyping, analysis of methylation patterns, restriction fragment length polymorphism assays, sequencing and PCR-based assays (including multiplex F-PCR STR analysis, whole genome amplification and microarray analysis), as well as other methods described below.

Chromosomal abnormalities, either in structure or number, can be detected by karyotyping which is well known in the art such as FISH. Karyotyping analysis is generally performed on nuclei which have been arrested during mitosis by the addition of a mitotic spindle inhibitor such as colchicine. Preferably, a Giemsa-stained chromosome spread is prepared, allowing analysis of chromosome number as well as detection of chromosomal translocations.

The genetic assays may involve any suitable method for identifying mutations or polymorphisms, such as: sequencing of the DNA at one or more of the relevant positions; differential hybridisation of an oligonucleotide probe designed to hybridise at the relevant positions of either the wild-type or mutant sequence; denaturing gel electrophoresis following digestion with an appropriate restriction enzyme, preferably following amplification of the relevant DNA regions; 51 nuclease sequence analysis; non-denaturing gel electrophoresis, preferably following amplification of the relevant DNA regions; conventional RFLP (restriction fragment length polymorphism) assays; selective DNA amplification using oligonucleotides which are matched for the wild-type sequence and unmatched for the mutant sequence or vice versa; or the selective introduction of a restriction site using a PCR (or similar) primer matched for the wild-type or mutant genotype, followed by a restriction digest. The assay may be indirect, ie capable of detecting a mutation at another position or gene which is known to be linked to one or more of the mutant positions. The probes and primers may be fragments of DNA isolated from nature or may be synthetic.

A non-denaturing gel may be used to detect differing lengths of fragments resulting from digestion with an appropriate restriction enzyme. The DNA is usually amplified before digestion, for example using the polymerase chain reaction (PCR) method and modifications thereof.

Amplification of DNA may be achieved by the established PCR methods or by developments thereof or alternatives such as quantitative PCR, quantitative fluorescent PCR (QF-PCR), multiplex ligation dependent probe amplification, digital PCR, real time PCR (RT-PCR), single nuclei PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

An "appropriate restriction enzyme" is one which will recognise and cut the wild-type sequence and not the mutated sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognises a sequence which occurs only rarely.

In another method, a pair of PCR primers are used which hybridise to either the wild-type genotype or the mutant genotype but not both. Whether amplified DNA is produced will then indicate the wild-type or mutant genotype (and hence phenotype).

A preferable method employs similar PCR primers but, as well as hybridising to only one of the wild-type or mutant sequences, they introduce a restriction site which is not otherwise there in either the wild-type or mutant sequences.

In order to facilitate subsequent cloning of amplified sequences, primers may have restriction enzyme sites appended to their 5' ends. Thus, all nucleotides of the primers are derived from the gene sequence of interest or sequences adjacent to that gene except the few nucleotides necessary to form a restriction enzyme site. Such enzymes and sites are well known in the art. The primers themselves can be synthesized using techniques which are well known in the art. Generally, the primers can be made using synthesizing machines which are commercially available.

PCR techniques that utilize fluorescent dyes may also be used to detect genetic defects in DNA from fetal nuclei isolated by the methods of the invention. These include, but are not limited to, the following five techniques.

i) Fluorescent dyes can be used to detect specific PCR amplified double stranded DNA product (e.g. ethidium bromide, or SYBR Green I).

ii) The 5' nuclease (TaqMan) assay can be used which utilizes a specially constructed primer whose fluorescence is quenched until it is released by the nuclease activity of the Taq DNA polymerase during extension of the PCR product.

iii) Assays based on Molecular Beacon technology can be used which rely on a specially constructed oligonucleotide that when self-hybridized quenches fluorescence (fluorescent dye and quencher molecule are adjacent). Upon hybridization to a specific amplified PCR product, fluorescence is increased due to separation of the quencher from the fluorescent molecule.

iv) Assays based on Amplifluor (Intergen) technology can be used which utilize specially prepared primers, where again fluorescence is quenched due to self-hybridization. In this case, fluorescence is released during PCR amplification by extension through the primer sequence, which results in the separation of fluorescent and quencher molecules.

v) Assays that rely on an increase in fluorescence resonance energy transfer can be used which utilize two specially designed adjacent primers, which have different fluorochromes on their ends. When these primers anneal to a specific PCR amplified product, the two fluorochromes are brought together. The excitation of one fluorochrome results in an increase in fluorescence of the other fluorochrome.

The acronym "FISH" references a technique that uses chromophore tags (fluorophores) that emit a secondary signal if illuminated with an excitation light to detect a chromosomal structure. FISH uses fluorescent probes which bind only to those parts of the chromosome with which they show a high degree of sequence similarity. Such tags may be directed to specific chromosomes and specific chromosome regions. The probe has to be long enough to hybridize specifically to its target (and not to similar sequences in the genome), but not too large to impede the hybridization process, and it should be tagged directly with fluorophores. This can be done in various ways, for example nick translation or PCR using tagged nucleotides. If signal amplification is necessary to exceed the detection threshold of the microscope (which depends on many factors such as probe labelling efficiency, the kind of probe and the fluorescent dye), secondary fluorescent tagged antibodies or streptavidin are bound to the tag molecules, thus amplifying the signal.

Fetal nuclei isolated using the methods of the invention can also be analysed using the MassARRAY® and SEQureDx™ procedures of Sequenom Technology (San Deigo, Calif., USA).

Fetal nuclei, or an enriched nuclei population of fetal nuclei, obtained using a method of the invention can be placed into wells of a microtitre plate (one nuclei per well) and analysed independently. Preferably, each nuclei will not only be screened for a trait(s) of interest, but screened to confirm/detect that the nuclei in a particular well is a fetal nuclei. In this instance, multiplex analysis can be performed as generally described by Findlay et al. (1996, 1998 and 2001).

The methods of the invention may include the step of fixing and permeabilizing the nuclei in the sample. Such procedures are known to those skilled in the art. For example, fixation may involve initial paraformaldehyde fixation followed by treatment with detergents such as Saponin, TWEEN-based detergents, Triton X-100, Nonidet NP40, NP40 substitutes, or other membrane disrupting detergents. Permeabilization may also involve treatment with alcohols (ethanol or methanol). Initial fixation may also be in ethanol. Combined fixation/permeabilization may also be performed using commercially available kits, including DAKO-Intrastain™, Caltag's Fix & Perm reagents, Ortho Diagnostic's Permeafix™. If required, methods for the extraction of DNA from fixed samples for genetic analysis are also known to those skilled in the art. For example, US 20040126796 discloses a method for the extraction of DNA from tissues and other samples, such as formalin-fixed tissue. The isolation of DNA from fixed samples for use in PCR has also been described by Lehman and Kreipe (2001) and Fitzgerald et al. (1993).

Kits

The present invention also provides kits for enriching fetal nuclei from a sample, the kit comprising at least two of the following;
i) an apparatus for obtaining the sample,
ii) an apparatus and/or media for transporting and/or storing the sample to a diagnostic laboratory,
iii) an apparatus for obtaining a second sample comprising maternal DNA but no fetal DNA from the mother,
iv) an apparatus for at least partially mechanically disaggregating the sample,
v) an enzyme for at least partially enzymatically disaggregating the sample,
vii) an antibody which binds fetal trophoblasts,
viii) a composition for performing complement mediated lysis,
ix) at least one apparatus or reagent for selecting fetal nuclei, and/or
x) a reagent(s) for performing a genetic assay.

In one example, the kit comprises at least two of the following;
i) an apparatus for obtaining the sample,
ii) an apparatus and/or media for transporting and/or storing the sample to a diagnostic laboratory,
iii) an apparatus for obtaining a second sample comprising maternal DNA but no fetal DNA from the mother,
iv) an apparatus for at least partially mechanically disaggregating the sample,
v) an enzyme for at least partially enzymatically disaggregating the sample,
vi) at least one apparatus or reagent for selecting fetal nuclei, and/or
vii) a reagent(s) for performing a genetic assay.

In one embodiment, the kit comprises
i) an apparatus for at least partially mechanically disaggregating the sample, and
ii) at least one reagent for selecting fetal nuclei using magnetic separation.

In an alternate embodiment, the kit comprises
i) an apparatus for at least partially enzymatically disaggregating the sample, and
ii) at least one apparatus for selecting fetal nuclei using size separation.

In a further embodiment, the kit comprises
i) an antibody which binds fetal trophoblasts, and
ii) a composition for performing complement mediated lysis.

Preferably, the apparatus for selecting fetal nuclei using size separation is a cell strainer.

In a further embodiment, the kit comprises an apparatus for obtaining the sample, an apparatus and/or media for transporting and/or storing the sample to a diagnostic laboratory.

The kit may further comprise components for analysing the genotype of a fetal nuclei, determining the father of a fetus, and/or determining the sex of the fetus.

Typically, the kits will also include instructions recorded in a tangible form (e.g., contained on paper or an electronic medium), for example, for using a packaged agent for enriching fetal nuclei from a sample. The instructions will typically indicate the reagents and/or concentrations of reagents and at least one enrichment method parameter which might be, for example, the relative amounts of agents to use per amount of sample. In addition, such specifics as maintenance, time periods, temperature and buffer conditions may also be included.

EXAMPLES

Example 1

Sample Preparation

A cervical mucus sample (transcervical sample) is collected using a fine, flexible aspiration catheter ("Aspiracath", Cook®; "Aspiration Kit", Medgyn Products; "Endosampler", Medgyn Products; "Goldstein Sonobiopsy Catheter", Cook®) or a brush ("Tao brush endometrial sampler", Cook®). The aspiration catheter is inserted approximately 2-3 cm into the cervix at the level of the internal os. A 0.5 to 1 ml sample is collected by gentle aspiration (or if using an endometrial brush, by gentle rotation). The catheter (or brush) is removed and the end of the device containing the sample is cut and placed in a sterile container for transport.

The sampling device is removed from the transport container using sterile forceps and transferred to an organ petri dish. The sample is washed from the device using Phosphate Buffered Saline (PBS). Complete removal sometimes requires manual assistance using sterile forceps. The sample is manually tweezed apart using sterile forceps into small pieces using sterile forceps. Gentle pipetting using a 1 ml pipette further disaggregates the sample.

The entire sample is then passed through a cell strainer (100 μm mesh size) into a sterile 50 ml FALCON™ tube. A further 3-ml PBS is passed through the strainer (making sure that all single cells have filtered through). The portion of sample passing through the strainer is largely a single cell/nuclei suspension. This contains a mixture of cell types including Syncytiotrophoblasts, Cytotrophoblasts, free fetal nuclei and maternal cells. The sample is now appropriate for use in cell sorting procedures.

The 50 ml FALCON™ tube containing cells <100 μm in size is centrifuged at 4000 rpm for 5 minutes and the cell pellet is resuspended in 1 ml PBS. An aliquot of the sample (thin layer) is placed onto a slide, air-dried and fixed. The slide is then stained with haematoxylin & eosin (H&E). Light microscopy is used to determine the presence/absence of syncytiotrophoblasts in the sample.

A total of 62 samples were used in this study. Samples were collected from women undergoing elective termination of pregnancy using different samplers during first trimester (5-12 weeks gestation).

Example 2

Isolation of Free Fetal Nuclei Using Immunomagnetic Sorting

Cells/nuclei from Example 1 are centrifuged at 4000 rpm for 5 min. The pellet is washed with 1 ml cold PBS containing 0.5% BSA and 0.5M EDTA, centrifuged and resuspended in 50 μl of cold PBS containing 0.5% BSA and 0.5M EDTA.

5 μl of anti-nuclear membrane protein (Millipore) or anti-lamin A and C monoclonal antibody (AbCam) is added and the cells incubated for 20 minutes at room temperature with rotation. The cells are washed twice with PBS containing 0.5% BSA and 0.5M EDTA to remove unbound antibody. The cells are then resuspended in 50 μl cold PBS containing 0.5% BSA and 0.5M EDTA.

5 μl of rat anti-mouse microbeads IgG (Miltenyi, Germany) are added. The cells are incubated for 20 minutes at room temperature with rotation. The cells are then washed twice with PBS containing 0.5% BSA and 0.5M EDTA to remove unbound antibody.

Cell sorting is achieved using a pre-cooled LS columns (Miltenyi, Germany) using the following procedure;

- Place a MACS separation pre-cooled LS cell column (Miltenyi Biotec) onto the separation unit (magnet).
- Place a sterile 15 ml FALCON™ tube directly underneath the column.
- Add 1 ml of the suspension to the column. Collect the unlabelled cells, which pass through.
- Wash out the 1.5 ml tube twice with 1 ml PBS containing 2 mM EDTA and 1% BSA to remove any cells remaining in tube and add them to the column.
- Once the column stops eluting buffer, remove the column from the separation unit and place it onto a new 15 ml FALCON™ collection tube. Discard the tube containing the unlabelled nuclei fraction.
- Pipette 2 ml of cold PBS containing 0.5% BSA and 0.5M EDTA onto the column.
- Immediately flush out the fraction with the magnetically labelled nuclei by firmly applying the plunger supplied with the column.
- Centrifuge the 15 ml tube containing "fetal positive" nuclei for 5 min at 4000 rpm.

This is a fetal nuclei-enriched fraction, which is now available for further analysis, for example, using PCR.

Example 3

Size Fractionation of Free Fetal Nuclei

Sample from Example 1 are centrifuged at 4000 rpm for 5 min. The pellet is washed with 1 ml cold PBS, centrifuged and resuspended in 1 ml of cold PBS. The entire sample is then passed through a cell strainer (40 μm mesh size) into a sterile 50 ml FALCON™ tube. A further 3-ml PBS is passed through the strainer (making sure that all single cells have filtered through). The portion of sample passing through the strainer is largely a single cell suspension which has been depleted of syncytial trophoblasts.

The eluted cell/nuclei suspension is further passed through a 8 μm pore-size "Nucleopore" track-etched membrane filter (Whatman). The eluted sample is centrifuged at 4000 rpm for 5 minutes and the pellet is resuspended in 1 ml PBS. An aliquot of the sample (thin layer) is placed onto a slide, air-dried and fixed. The slide is then stained with haematoxylin & eosin (H&E). Light microscopy is used to determine the presence/absence of free nuclei in the sample (FIG. 1).

The nuclei-enriched fraction is now available for further analysis using, for example, PCR.

Example 4

Fluorescent Multiplex PCR Analysis

All samples were subjected to multiplex QF-PCR using four short tandem repeat (STR) markers on chromosome 21 (D21S11, D21S1413, D21S1437 and D21S1442) and two sex chromosome markers (hypoxanthine guanine phosphoribosyl transferase (HPRT) and amelogenin X and Y) to simultaneously determine the sex of the isolated fetal nuclei.

STR profiles were derived following analysis of the PCR products on a 3130 Genetic Analyser (Applied Biosystems) using Genescan version 3.7 software. Maternal contamination in the sample was determined via allelic differentiation using targeted STR markers on chromosome 21. Comparison of the enriched fetal nuclei and maternal STR profiles confirmed fetal origin and the presence or absence of maternal cell contamination in the sample. Samples which were pure fetal were expected to show two allelic peaks for each STR marker, one shared with the mother and the other inherited from the father.

Following PCR analysis, the results were compared with the histological data for the presence/absence of fetal DNA in these samples. Both lamin and anti-nuclear membrane protein antibodies allowed the isolation of pure fetal nuclei DNA profiles to be obtained (FIGS. 2 and 3).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/171,334 filed 21 Apr. 2009, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Adinolphi and Sherlock (1997) Hum Reprod Update. 3: 383-392.
Adinolphi et al. (1995a) Prenat Diagn 15: 35-39.
Adinolphi et al (1995b) Prenat Diagn. 15: 943-949.
Al-Multi et al. (1999) Am. J. Med. Genet. 85:66-75.
Antalis and Godbolt (1991) Nucl Acids Res 19: 4301.
Bauer et al. (2002) Int. J. Legal Med. 116:39-42.
Bischoff and Simpson (2006) 18:206-220.
Bulmer et al (1995) Prenat Diagn 15: 1143-1153.
Bussani et al. (2002) Prenat Diagn. 22: 1098-1101.
Bussani et al. (2004) Mol Diagn. 8:259-63.
Bussani et al. (2007) Mol Diagn Ther. 11:117-121.
Cioni et al. (2003) Prenat Diagn 23: 168-171.
Daryanii et al. (1997) Prenat Diagn. 17: 243-248.
Fejgin et al. (2001) Prenat Diagn. 21: 619-621.
Findlay et al. (1996) Hum Reprod Update 2: 137-152.
Findlay et al. (1998) J Clin Pathol Mol Pathol 51: 164-167.
Findlay et al. (2001) Mol Cellul Endocrinol 183: S5-S12.
Fitzgerald et al. (1993) Biotechniques 15:128-133.
Goldberg et al. (1980) Am J Obstet Gynecol 138:436-440.
Hymer and Cuff (1963) J Histochem Cytochem 12: 359-363.
Inglis et al. (2008) J Immunological Methods 329: 151-156.
Katz-Jaffe et al. (2005) BJOG 112: 595-600.
Kingdom et al. (1995) Obstet Gynecol. 86: 283-288.
Krishan and Dandekar (2005) J Histochem Cytochem 53: 1033-1036.
Lehman and Kreipe (2001) Methods 25:409-418.
Mantzaris et al. (2005) Aus NZ J Obstet Gynaecol. 45: 529-532.
Massari et al. (1996) Hum Genet. 97: 150-155.
Michalet et al. (2005) Science 307:538-544.
Miller et al. (1999) Hum Reprod. 14: 521-531.
Murthy et al. (2006) Biomed Microdevices 8:231-237.
Rhine et al. (1975) Am J Obste Gynecol. 122: 155-160.
Rhine et al. (1977) Birth Defects Orig Artic Ser. 13: 231-247.
Rodeck et al. (1995). Prenat Diagn. 15: 933-942.
Shettles (1971) Nature 230: 52-53.
Tokumasu and Dvorak (2003) J. Microsc. 211:256-261.
Tutschek et al. (1995) Prenat Diagn 15: 951-960.
Wu et al. (2007) J Micromech Microeng 17:1992-1999.

What is claimed is:

1. A method of enriching free fetal nuclei from a cervical mucous sample, comprising size-selecting cellular material which is less than about 10 μm in size from a cervical mucous sample from a pregnant female, wherein the cervical mucous sample comprises intact maternal cells, intact fetal cells, and free fetal nuclei and wherein the cervical mucous sample is partially disaggregated prior to the size-selecting, thereby enriching the free fetal nuclei in the selected cellular material which is less than about 10 μm in size.

2. The method of claim 1 which comprises selecting cellular material which is less than about 8 μm in size.

3. The method of claim 1, wherein the cellular material is selected using at least one method selected from the group consisting of a cell strainer, flow cytometry, and microfluidics.

4. The method of claim 1, wherein the cervical mucous sample is partially mechanically and/or enzymatically disaggregated prior to the size-selecting.

5. The method of claim 4, wherein partially mechanically disaggregating the sample comprises gentle pipetting using an about 1 ml pipette and/or tweezing the sample apart using forceps.

6. The method of claim 4, wherein partially enzymatically disaggregating the sample comprises contacting the sample with a collagenase, a protease or a combination thereof.

7. The method of claim 1, further comprising selecting fetal cells.

8. The method of claim 7, wherein the method further comprises:
   i) at least partially mechanically disaggregating the sample to produce a cellular material suspension;
   ii) filtering the suspension through a first cell strainer which has a mesh size of at least about 100 μm and collecting the cellular material that passed through the first cell strainer;
   iii) filtering the cellular material collected in step ii) through a second cell strainer which has a mesh size of less than about 40 μm and collecting the cellular material that did not pass through the second cell strainer, and independently collecting the cellular material that passed through the second cell strainer;
   iv) filtering the cellular material that passed through the second cell strainer collected in step iii), through a third cell strainer which has a mesh size of less than about 10

μm and collecting the cellular material that passed through the third cell strainer; and v) combining the cellular material that did not pass through the second cell strainer in step iii), which comprises fetal cells of a size greater than the mesh size of less than about 40 μm, with the cellular material that passed through the third cell strainer in step iv), which comprises fetal nuclei of a size less than the mesh size of less than about 10 μm.

9. The method of claim 7, wherein the method further comprises:
   i) at least partially enzymatically disaggregating the sample to produce a cellular material suspension;
   ii) filtering the suspension through a first cell strainer which has a mesh size of less than about 40 μm and collecting the cellular material that did not pass through the first cell strainer, and independently collecting the cellular material that passed through the first cell strainer;
   iii) filtering the cellular material that passed through the first cell strainer in step ii), through a second cell strainer which has a mesh size of less than about 10 μm and collecting the cellular material that passed through the second cell strainer; and
   iv) combining the cellular material that did not pass through the first cell strainer in step ii), which comprises fetal cells of a size greater than the mesh size of less than about 40 μm, with the cellular material that passed through the second cell strainer in step iii), which comprises fetal nuclei of a size less than the mesh size of less than about 10 μm.

10. The method of claim 7, wherein the method further comprises:
    i) at least partially mechanically disaggregating the sample to produce a cellular material suspension;
    ii) filtering the suspension through a cell strainer which has a mesh size of at least about 100 μm and collecting the cellular material that passed through the cell strainer;
    iii) sorting the cellular material that passed through the cell strainer in step ii) by fluorescent activated cell separation (FACS) based on forward scatter and collecting cellular material which is at least about 40 μm in size;
    iv) sorting the cellular material that passed through the cell strainer in step ii) and/or the cellular material which is at least about 40 μm in size, collected in step iii), by fluorescent activated cell separation (FACS) based on forward scatter and collecting cellular material which is less than about 10 μm; and
    v) combining the cellular material that is at least about 40 μm in size, collected in step iii) and which comprises fetal cells, with the cellular material that is less than about 10 μm, collected in step iv), and which comprises fetal nuclei.

11. The method of claim 7, wherein the method further comprises:
    i) at least partially mechanically and/or enzymatically disaggregating the sample to produce a cellular material suspension;
    ii) sorting the suspension by fluorescent activated cell separation (FACS) based on forward scatter and collecting cellular material which is between about 40 μm and 100 μm in size, and collecting cellular material which is less than about 10 μm; and
    iii) combining the cellular material which is between about 40 μm and 100 μm in size, which comprises fetal cells, with the cellular material which is less than about 10 μm and which comprises fetal nuclei.

12. The method of claim 7 which comprises positively selecting fetal cells using an agent which binds fetal cells but not maternal cells.

13. The method of claim 7, wherein the step of selecting comprises negatively selecting fetal cells using an agent which binds maternal cells but does not bind fetal cells.

14. The method of claim 13 where the method further comprises combining the fetal nuclei and fetal cells.

15. The method of claim 1, wherein the sample was obtained within 5 to 18 weeks of pregnancy.

16. The method of claim 1 wherein the sample is obtained from a pregnant female prior to the step of selecting.

17. The method of claim 1, wherein the cellular material is selected using a cell strainer or flow cytometry.

18. The method of claim 1, wherein the cellular material is selected using a cell strainer.

19. A method of enriching fetal cells and free fetal nuclei, comprising:
    i) at least partially mechanically and/or enzymatically disaggregating a cervical mucous sample from a pregnant female to produce a cellular material suspension comprising intact maternal cells, intact fetal cells and free fetal nuclei;
    ii) filtering the suspension through a first cell strainer which has a mesh size of at least about 100 μm and collecting the cellular material that passed through the first cell strainer;
    iii) filtering the cellular material collected in step ii) through a second cell strainer which has a mesh size of less than about 40 μm and collecting the cellular material that did not pass through the second cell strainer, and independently collecting the cellular material that passed through the second cell strainer;
    iv) filtering the cellular material that passed through the second cell strainer collected in step iii), through a third cell strainer which has a mesh size of less than about 10 μm and collecting the cellular material that passed through the third cell strainer; and
    v) combining the cellular material that did not pass through the second cell strainer in step iii), which comprises fetal cells of a size greater than the mesh size of less than about 40 μm, with the cellular material that passed through the third cell strainer in step iv), which comprises fetal nuclei of a size less than the mesh size of less than about 10 μm; whereby the fetal cells and the free fetal nuclei are enriched.

* * * * *